(12) United States Patent
Dolezal et al.

(10) Patent No.: US 10,100,077 B2
(45) Date of Patent: Oct. 16, 2018

(54) 6-ARYL-9-GLYCOSYLPURINES AND USE THEREOF

(71) Applicant: UNIVERZITA PALACKEHO V OLOMOUCI, Olomouc (CZ)

(72) Inventors: Karel Dolezal, Hlubocky (CZ); Lucie Plihalova, Olomouc (CZ); Hana Vylicilova, Olomouc (CZ); Marek Zatloukal, Sumperk (CZ); Ondrej Plihal, Olomouc (CZ); Jiri Voller, Brno-Bystrc (CZ); Miroslav Strnad, Olomouc (CZ); Magdalena Bryksova, Bystrovany (CZ); Jitka Vostalova, Kozusany-Tazaly (CZ); Alena Rajnochova Svobodova, Olomouc (CZ); Jitka Ulrichova, Olomouc (CZ); Lukas Spichal, Olomouc (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 15/527,613

(22) PCT Filed: Sep. 14, 2015

(86) PCT No.: PCT/CZ2015/050005
§ 371 (c)(1),
(2) Date: May 17, 2017

(87) PCT Pub. No.: WO2016/091235
PCT Pub. Date: Jun. 16, 2016

(65) Prior Publication Data
US 2017/0334943 A1    Nov. 23, 2017

(30) Foreign Application Priority Data
Dec. 9, 2014   (CZ) ..................... 2014-875

(51) Int. Cl.
| | |
|---|---|
| *C07H 19/19* | (2006.01) |
| *C07H 19/173* | (2006.01) |
| *A61K 8/60* | (2006.01) |
| *A61K 31/7076* | (2006.01) |
| *A61Q 17/04* | (2006.01) |
| *A61Q 19/08* | (2006.01) |
| *C07H 19/16* | (2006.01) |

(52) U.S. Cl.
CPC ............. *C07H 19/16* (2013.01); *A61K 8/606* (2013.01); *A61K 31/7076* (2013.01); *A61Q 17/04* (2013.01); *A61Q 19/08* (2013.01); *C07H 19/173* (2013.01); *C07H 19/19* (2013.01)

(58) Field of Classification Search
CPC ...... C07H 19/16; C07H 19/19; C07H 19/173; A61K 8/60; A61K 31/7076; A61Q 17/04; A61Q 19/08

USPC .............. 544/264; 514/263.2; 424/70.9; 536/27.2, 27.4
See application file for complete search history.

(56) References Cited

U.S. PATENT DOCUMENTS

| | | |
|---|---|---|
| 6,294,522 B1 | 9/2001 | Zablocki et al. |
| 2008/0131952 A1 | 6/2008 | Wu et al. |
| 2013/0045942 A1* | 2/2013 | Shi ................. C07D 473/34 514/46 |

FOREIGN PATENT DOCUMENTS

| | | |
|---|---|---|
| EP | 2657246 A1 | 10/2013 |
| WO | 2004058791 A2 | 7/2004 |
| WO | 2012084173 A2 | 6/2012 |

OTHER PUBLICATIONS

McCrane et al. Chem. Res. Toxicol. 2014, 27, 1282-1293.*
Veldhuzen et al. J. Am. Chem. Soc. 2001, 123, 11126-11132.*
Pccompound—CID 2588066—Create Date May 27, 2009.*
Pccompound—CID 15217054—Create Date Feb. 9, 2007.*
Pccompound—CID 72747589—Create Date Feb. 18, 2014.*
Pccompound—selected items 1-16, Create Date Mar. 25, 2005 to Mar. 21, 2013.*
Pccompound—selected items 1-37, Create Date Mar. 26, 2005 to Sep. 16, 2014.*
International Search Report and Written Opinion for corresponding PCT application No. PCT/CZ2015/050005.

* cited by examiner

*Primary Examiner* — Venkataraman Balasubramanian
(74) *Attorney, Agent, or Firm* — Notaro, Michalos & Zaccaria P.C.

(57) ABSTRACT

6-aryl-9-glycosidpurines of general formula I and pharmaceutically acceptable salts thereof with alkali metals, ammonia, amines, or addition salts with acids, wherein
Gly represents β-D-arabinofuranosyl or β-D-2'-deoxyribofuranosyl,
Ar represents benzyl or furfuryl, each of which can be unsubstituted or substituted by one or more, preferably one to three, substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, for use as antisenescent and UV protective compounds in animals.

10 Claims, 3 Drawing Sheets

6-ARYL-9-GLYCOSYLPURINES AND USE THEREOF

FIELD OF ART

The invention relates to 6-(benzylamino/furfurylamino)-9-β-D-arabinofuranosylpurine or -β-D-2'-deoxyribofuranosylpurine derivatives which slow down the aging of animal and human cells and which show UV photoprotective properties.

BACKGROUND ART

Substituted adenine derivatives are known as phytohormones. The range of their properties is rather broad, especially known is their anti-tumor and pro-apoptotic activity, i.e., activities relating to inhibition of tumor cell growth. Several glycosylated derivatives were prepared, in particular ribosylated derivatives. An arabinosylated derivative prepared so far was 6-benzylamino-9-arabinosylpurine which was published as a compound participating in inhibition of replication of tobacco mosaic virus in extirpated leaves Nicotiana glutinosa (Barai et al. Vestsi Akademii Nauk Belarusi 1: 18-22, 1992). 6-chloropurine arabinoside was prepared from 6-chloropurine riboside and its antiviral activity was explored (Maruyama et al. Chem. Pharm. Bull. 44: 2331-2334, 1996). Several methylated derivatives of 6-(benzylamino)-9-β-D-arabinofuranosylpurine were prepared for antiviral activity testing, and their activity in killing Vaccinia virus and Herpes simplex virus was tested. No effect was observed for benzylamino derivative, neither for 2-methylbenzyl, 3-methylbenzyl, 2,3-dimethylbenzyl, 2,6-dimethylbenzyl, 3,4-dimethylbenzyl derivatives. A low activity against Vaccinia virus, strain IHD, was observed for 2,4-dimethylbenzyl and 2,5-dimethylbenzyl substituents (Masakatsu et al. Chem. Pharm. Bull. 25: 2482-2489, 1977). Some N6-substituted derivatives of adenine arabinoside were prepared as selective inhibitors of varicella-zoster virus, the substituents were 6-methylamino, 6-dimethylamino-, 6-ethylamino-, 6-N-ethylmethylamino-, NN-diethylamino-, 6-n-propylamino-, 6-isopropylamino-, 6-n-hexylamino-, 6-cyclohexylamino-, 6-anilino (Koszalka et al. Antimicrob. Agents Chemother. 35: 1437-1443, 1991).

The object of the present invention are glycosylated derivatives of adenine with antisenescent and photoprotective properties which show extremely low or no toxicity and high activity in aging, cell division and differentiation processes and photoprotection.

DISCLOSURE OF THE INVENTION

Object of the invention is use of 6-aryl-9-glycosylpurines of general formula I

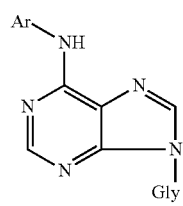

and pharmaceutically acceptable salts thereof with alkali metals, ammonia, amines, or addition salts with acids, wherein Gly represents β-D-arabinofuranosyl or β-D-2'-deoxyribofuranosyl, Ar represents benzyl or furfuryl, each of which can be unsubstituted or substituted by one or more, preferably one to three, substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, for regulation, in particular inhibition, of aging in animals, in particular mammals, for cosmetic purposes, and/or for UV photoprotection of animals, in particular mammals, for cosmetic purposes.

The invention further encompasses the 6-aryl-9-glycosylpurines of general formula I for use in a method of regulation, in particular inhibition, of aging in animals, in particular mammals, for therapeutic purposes, and/or for UV photoprotection of animals, in particular mammals, for therapeutic purposes.

Another object of the invention is a method for regulating aging and/or UV photodamage of microorganisms, and animal cells in vitro, in which at least one compound of general formula I is applied to the plant or cells or microorganisms.

If not stated otherwise, then:

alkyl represents a linear or branched C1-C6, preferably C1-C4, alkyl chain, acyl represents an acyl group having 2 to 6 carbon atoms, halogen represents a halogen atom selected from the group consisting of fluorine, bromine, chlorine and iodine atom, sulfo represents $-SO_3R_c$, wherein $R_c$ represents hydrogen atom, linear or branched alkyl, alkenyl or alkynyl group containing 1 to 6 carbon atoms, sulfoamido represents $-NHSO_3R_d$, wherein $R_d$ represents hydrogen atom, linear or branched alkyl group containing 1 to 6 carbon atoms.

Particularly preferred compounds of the invention are the compounds of formula I selected from the group consisting of: 6-furfurylamino-9-β-D-arabinofuranosylpurine, 6-(3-methylfurfurylamino)-9-β-D-arabinofuranosylpurine, 6-(4-methylfurfurylamino)-9-β-D-arabinofuranosylpurine, 6-(5-methylfurfurylamino)-9-β-D-arabinofuranosylpurine, 6-(3-fluorofurfurylamino)-9-β-D-arabinofuranosylpurine, 6-(4-fluorofurfurylamino)-9-β-D-arabinofuranosylpurine, 6-(5-fluorofurfurylamino)-9-β-D-arabinofuranosylpurine, 6-(3-chlorofurfurylamino)-9-β-D-arabinofuranosylpurine, 6-(4-chlorofurfurylamino)-9-β-D-arabinofuranosylpurine, 6-(5-chlorofurfurylamino)-9-β-D-arabinofuranosylpurine, 6-(3-bromofurfurylamino)-9-β-D-arabinofuranosylpurine, 6-(4-bromofurfurylamino)-9-β-D-arabinofuranosylpurine, 6-(5-bromofurfurylamino)-9-β-D-arabinofuranosylpurine, 6-(3-hydroxyfurfurylamino)-9-β-D-arabinofuranosylpurine, 6-(4-hydroxyfurfurylamino)-9-β-D-arabinofuranosylpurine, 6-(5-hydroxyfurfurylamino)-9-β-D-arabinofuranosylpurine, 6-(3-methoxyfurfurylamino)-9-β-D-arabinofuranosylpurine, 6-(4-methoxyfurfurylamino)-9-β-D-arabinofuranosylpurine, 6-(5-methoxyfurfurylamino)-9-β-D-arabinofuranosylpurine, 6-(2-aminofurfurylamino)-9-β-D-arabinofuranosylpurine, 6-(3-aminofurfurylamino)-9-β-D-arabinofuranosylpurine, 6-(4-aminofurfurylamino)-9-β-D-arabinofuranosylpurine, 6-(3,4-dihydroxyfurfurylamino)-9-β-D-arabinofuranosylpurine, 6-(3,5-dihydroxyfurfurylamino)-9-β-D-arabinofuranosylpurine, 6-(3,4-dihydroxyfurfurylamino)-9-β-D-arabinofuranosylpurine, 6-(2,4-dihydroxyfurfurylamino)-9-β-D-arabinofuranosylpurine, 6-(2,5-dihydroxyfurfurylamino)-9-β-D-arabinofuranosylpurine, 6-(2,6-dihydroxyfurfurylamino)-9-β-D-arabinofuranosylpurine, 6-(3,4-dimethoxyfurfurylamino)-9-β-D-arabinofuranosylpurine, 6-(3,4-dimethoxyfurfurylamino)-9-β-D-arabinofuranosylpurine, 6-(3,5-dimethoxyfurfurylamino)-9-β-D-arabinofuranosylpurine, 6-(2,3-dimethoxyfurfurylamino)-9-β-D-arabinofuranosylpurine, 6-(2,4-dimethoxyfurfurylamino)-9-β-D-arabinofuranosylpurine, 6-(2,5-dimethoxyfurfurylamino)-9-β-D-arabinofuranosylpurine, 6-(2,6-dimethoxyfurfurylamino)-9-β-D-arabinofuranosylpurine, 6-(2-hydroxy-3-methoxyfurfurylamino)-9-β-D-arabinofuranosylpurine, 6-(2-hydroxy-4-methoxyfurfurylamino)-9-β-D-arabinofuranosylpurine, 6-(2-hydroxy-5-methoxyfurfurylamino)-9-β-D-arabinofuranosylpurine, 6-(2-hydroxy-6-methoxyfurfurylamino)-9-β-D-arabinofuranosylpurine, 6-(3-hydroxy-2-methoxyfurfurylamino)-9-β-D-arabinofuranosylpurine, 6-(3-hydroxy-4-methoxyfurfurylamino)-9-β-D-arabinofuranosylpurine, 6-(3-hydroxy-5-methoxyfurfurylamino)-9-β-D-arabinofuranosylpurine, 6-(3-hydroxy-6-methoxyfurfurylamino)-9-β-D-arabinofuranosylpurine, 6-(4-hydroxy-2-methoxyfurfurylamino)-9-β-D-arabinofuranosylpurine, 6-(4-hydroxy-3-methoxyfurfurylamino)-9-β-D-arabinofuranosylpurine, 6-(4-hydroxy-5-methoxyfurfurylamino)-9-β-D-arabinofuranosylpurine, 6-(4-hydroxy-6-methoxyfurfurylamino)-9-β-D-arabinofuranosylpurine, 6-(2-fluorobenzylamino)-9-(3-D-arabinofuranosylpurine, 6-(3-fluorobenzylamino)-9-β-D-arabinofuranosylpurine, 6-(4-fluorobenzylamino)-9-β-D-arabinofuranosylpurine, 6-(2-bromobenzylamino)-9-β-D-arabinofuranosylpurine, 6-(3-bromobenzylamino)-9-β-D-arabinofuranosylpurine, 6-(4-bromobenzylamino)-9-β-D-arabinofuranosylpurine, 6-(2-iodobenzylamino)-9-β-D-arabinofuranosylpurine, 6-(3-iodobenzylamino)-9-β-D-arabinofuranosylpurine, 6-(4-iodobenzylamino)-9-β-D-arabinofuranosylpurine, 6-(2-chlorobenzylamino)-9-β-D-arabinofuranosylpurine, 6-(2-chlorobenzylamino)-9-β-D-arabinofuranosylpurine, 6-(3-chlorobenzylamino)-9-β-D-arabinofuranosylpurine, 6-(4-chlorobenzylamino)-9-β-D-arabinofuranosylpurine, 6-(2-methoxybenzylamino)-9-β-D-arabinofuranosylpurine, 6-(3-methoxybenzylamino)-9-β-D-arabinofuranosylpurine, 6-(4-methoxybenzylamino)-9-β-D-arabinofuranosylpurine, 6-(2-hydroxybenzylamino)-9-β-D-arabinofuranosylpurine, 6-(3-hydroxybenzylamino)-9-β-D-arabinofuranosylpurine, 6-(4-hydroxybenzylamino)-9-β-D-arabinofuranosylpurine, 6-(4-hexylbenzylamino)-9-β-D-arabinofuranosylpurine, 6-(2-fluoro-6-(trifluoromethyl)benzylamino)-9-β-D-arabinofuranosylpurine, 6-(3-chloro-2,6-difluorobenzylamino)-9-β-D-arabinofuranosylpurine, 6-(3-(trifluoromethylthio)benzylamino)-9-β-D-arabinofuranosylpurine, 6-(2-chloro-3,6-difluorobenzylamino)-9-β-D-arabinofuranosylpurine, 6-(4-(trifluoromethylthio)benzylamino)-9-β-D-arabinofuranosylpurine, 6-(3-fluoro-5-(trifluoromethyl)benzylamino)-9-β-D-arabinofuranosylpurine, 6-(2-chloro-4-fluorobenzylamino)-9-β-D-arabinofuranosylpurine, 6-(2-(trifluoromethoxy)benzylamino)-9-β-D-arabinofuranosylpurine, 6-(3-(trifluoromethyl)benzylamino)-9-β-D-arabinofuranosylpurine, 6-(2-(trifluoromethyl)benzylamino)-9-β-D-arabinofuranosylpurine, 6-(4-(trifluoromethyl)benzylamino)-9-β-D-arabinofuranosylpurine, 6-(4-chloro-3-(trifluoromethyl)benzylamino)-9-β-D-arabinofuranosylpurine, 6-(4-fluoro-3-(trifluoromethyl)benzylamino)-9-β-D-arabinofuranosylpurine, 6-(3,5-bis(trifluoromethyl)benzylamino)-9-β-D-arabinofuranosylpurine, 6-(3-(trifluoromethoxy)benzylamino)-9-β-D-arabinofuranosylpurine, 6-(4-(trifluoromethoxy)benzylamino)-9-β-D-arabinofuranosylpurine, 6-(4-(trifluoromethyl)benzylamino)-9-β-D-arabinofuranosylpurine, 6-(2-aminobenzylamino)-9-β-D-arabinofuranosylpurine, 6-(3-aminobenzylamino)-9-β-D-arabinofuranosylpurine, 6-(4-aminobenzylamino)-9-β-D-arabinofuranosylpurine, 6-(4-diethylaminobenzylamino)-9-β-D-arabinofuranosylpurine, 6-(3,4-dihydroxybenzylamino)-9-β-D-arabinofuranosylpurine, 6-(3,5-dihydroxybenzylamino)-9-β-D-arabinofuranosylpurine, 6-(3,4-dihydroxybenzylamino)-9-β-D-arabinofuranosylpurine, 6-(2,4-dihydroxybenzylamino)-9-β-D-arabinofuranosylpurine, 6-(2,5-dihydroxybenzylamino)-9-β-D-arabinofuranosylpurine, 6-(2,6-dihydroxybenzylamino)-9-β-D-arabinofuranosylpurine, 6-(3,4-dimethoxybenzylamino)-9-β-D-arabinofuranosylpurine, 6-(3,4-dimethoxybenzylamino)-9-β-D-arabinofuranosylpurine, 6-(3,5-dimethoxybenzylamino)-9-β-D-arabinofuranosylpurine, 6-(2,3-dimethoxybenzylamino)-9-β-D-arabinofuranosylpurine, 6-(2,4-dimethoxybenzylamino)-9-β-D-arabinofuranosylpurine, 6-(2,5-dimethoxybenzylamino)-9-β-D-arabinofuranosylpurine, 6-(2,6-dimethoxybenzylamino)-9-β-D-arabinofuranosylpurine, 6-(2-hydroxy-3-methoxybenzylamino)-9-β-D-arabinofuranosylpurine, 6-(2-hydroxy-4-methoxybenzylamino)-9-β-D-arabinofuranosylpurine, 6-(2-hydroxy-5-methoxybenzylamino)-9-β-D-arabinofuranosylpurine, 6-(2-hydroxy-6-methoxybenzylamino)-9-β-D-arabinofuranosylpurine, 6-(3-hydroxy-2-methoxybenzylamino)-9-β-D-arabinofuranosylpurine, 6-(3-hydroxy-4-methoxybenzylamino)-9-β-D-arabinofuranosylpurine, 6-(3-hydroxy-5-methoxybenzylamino)-9-β-D-arabinofuranosylpurine, 6-(3-hydroxy-6-methoxybenzylamino)-9-β-D-arabinofuranosylpurine, 6-(4-hydroxy-2-methoxybenzylamino)-9-β-D-arabinofuranosylpurine, 6-(4-hydroxy-3-methoxybenzylamino)-9-β-D-arabinofuranosylpurine, 6-(4-hydroxy-5-methoxybenzylamino)-9-β-D-arabinofuranosylpurine, 6-(4-hydroxy-6-methoxybenzylamino)-9-β-D-arabinofuranosylpurine, 6-(2,3,4-trimethoxybenzylamino)-9-β-D-arabinofuranosylpurine, 6-(2,4,5-trimethoxybenzylamino)-9-β-D-arabinofuranosylpurine, 6-(2,4,6-trimethoxybenzylamino)-9-β-D-arabinofuranosylpurine, 6-(3,4,5-trimethoxybenzylamino)-9-β-D-arabinofuranosylpurine, 6-(2-hydroxy-3,4,5-trimethoxybenzylamino)-9-β-D-arabinofuranosylpurine, 6-(2-hydroxy-3,4,6-trimethoxybenzylamino)-9-β-D-arabinofuranosylpurine, 6-(2-hydroxy-4,5,6-trimethoxybenzylamino)-9-β-D-arabinofuranosylpurine, 6-(2,4,6-trimethoxybenzylamino)-9-β-D-arabinofuranosylpurine, 6-(2,3,4-trihydroxybenzylamino)-9-β-D-arabinofuranosylpurine, 6-(2,4,6-trihydroxybenzylamino)-9-β-D-arabinofuranosylpurine, 6-(2,3,4-trihydroxybenzylamino)-9-β-D-arabinofuranosylpurine, 6-(3,4,5-trihydroxybenzylamino)-9-β-D-arabinofuranosylpurine, 6-(2,4,6-trihydroxybenzylamino)-9-β-D-arabinofuranosylpurine, 6-(2-hydroxy-3-chlorobenzylamino)-9-β-D-arabinofuranosylpurine, 6-(2-hydroxy-4-chlorobenzylamino)-9-β-D-arabinofuranosylpurine, 6-(2-hydroxy-5-chlorobenzylamino)-9-β-D-arabinofuranosylpurine, 6-(2-hydroxy-6-chlorobenzylamino)-9-β-D-arabinofuranosylpurine, 6-(2-hydroxy-3-iodobenzylamino)-9-β-D-arabinofuranosylpurine, 6-(2-hydroxy-4-iodobenzylamino)-9-β-D-arabinofuranosylpurine, 6-(2-hydroxy-5-iodobenzylamino)-9-β-D- arabinofuranosylpurine, 6-(2-hydroxy-6-iodobenzylamino)-9-β-D-arabinofuranosylpurine, 6-(2-hydroxy-3-bromobenzylamino)-9-β-D-arabinofuranosylpurine, 6-(2-hydroxy-4-bromobenzylamino)-9-β-D-arabinofuranosylpurine, 6-(2-hydroxy-5-bromobenzylamino)-9-β-D-arabinofuranosylpurine, 6-(2-hydroxy-6-bromobenzylamino)-9-β-D-arabinofuranosylpurine, 6-(2-hydroxy-3-fluorobenzylamino)-9-β-D-arabinofuranosylpurine, 6-(2-hydroxy-4-fluorobenzylamino)-9-β-D-arabinofuranosylpurine, 6-(2-hydroxy-5-fluorobenzylamino)-9-β-D-arabinofuranosylpurine, 6-(3-methylfurfurylamino)-9-β-D-2'-deoxyribofuranosylpurine, 6-(4-methylfurfurylamino)-9-β-D-2'-deoxyribofuranosylpurine, 6-(5-methylfurfurylamino)-9-β-D-2'-deoxyribofuranosylpurine, 6-(3-fluorofurfurylamino)-9-β-D-2'-deoxyribofuranosylpurine, 6-(4-fluorofurfurylamino)-9-β-D-2'-deoxyribofuranosylpurine, 6-(5-fluorofurfurylamino)-9-β-D-2'-deoxyribofuranosylpurine, 6-(3-chlorofurfurylamino)-9-β-D-2'-deoxyribofuranosylpurine, 6-(4-chlorofurfurylamino)-9-β-D-2'-deoxyribofuranosylpurine, 6-(5-chlorofurfurylamino)-9-β-D-2'-deoxyribofuranosylpurine, 6-(3-bromo-furfurylamino)-9-β-D-2'-deoxyribofuranosylpurine, 6-(4-bromofurfurylamino)-9-β-D-2'-deoxyribofuranosylpurine, 6-(5-bromofurfurylamino)-9-β-D-2'-deoxyribofuranosylpurine, 6-(3-hydroxyfurfurylamino)-9-β-D-2'-deoxyribofuranosylpurine, 6-(4-hydroxyfurfurylamino)-9-β-D-2'-deoxyribofuranosylpurine, 6-(5-hydroxyfurfurylamino)-9-β-D-2'-deoxyribofuranosylpurine, 6-(3-methoxyfurfurylamino)-9-β-D-2'-deoxyribofuranosylpurine, 6-(4-methoxyfurfurylamino)-9-β-D-2'-deoxyribofuranosylpurine, 6-(5-methoxyfurfurylamino)-9-β-D-2'-deoxyribofuranosylpurine, 6-(2-aminofurfurylamino)-9-β-D-2'-deoxyribofuranosylpurine, 6-(3-aminofurfurylamino)-9-β-D-2'-deoxyribofuranosylpurine, 6-(4-aminofurfurylamino)-9-β-D-2'-deoxyribofuranosylpurine, 6-(3,4-dihydroxyfurfurylamino)-9-β-D-2'-deoxyribofuranosylpurine, 6-(3,5-dihydroxyfurfurylamino)-9-β-D-2'-deoxyribofuranosylpurine, 6-(3,4-dihydroxyfurfurylamino)-9-β-D-2'-deoxyribofuranosylpurine, 6-(2,4-dihydroxyfurfurylamino)-9-β-D-2'-deoxyribofuranosylpurine, 6-(2,5-dihydroxyfurfurylamino)-9-β-D-2'-deoxyribofuranosylpurine, 6-(2,6-dihydroxyfurfurylamino)-9-β-D-2'-deoxyribofuranosylpurine, 6-(3,4-dimethoxyfurfurylamino)-9-β-D-2'-deoxyribofuranosylpurine, 6-(3,4-dimethoxyfurfurylamino)-9-β-D-2'-deoxyribofuranosylpurine, 6-(3,5-dimethoxyfurfurylamino)-9-β-D-2'-deoxyribofuranosylpurine, 6-(2,3-dimethoxyfurfurylamino)-9-β-D-2'-deoxyribofuranosylpurine, 6-(2,4-dimethoxyfurfurylamino)-9-β-D-2'-deoxyribofuranosylpurine, 6-(2,5-dimethoxyfurfurylamino)-9-β-D-2'-deoxyribofuranosylpurine, 6-(2,6-dimethoxyfurfurylamino)-9-β-D-2'-deoxyribofuranosylpurine, 6-(2-hydroxy-3-methoxyfurfurylamino)-9-β-D-2'-deoxyribofuranosylpurine, 6-(2-hydroxy-4-methoxyfurfurylamino)-9-β-D-2'-deoxyribofuranosylpurine, 6-(2-hydroxy-5-methoxyfurfurylamino)-9-β-D-2'-deoxyribofuranosylpurine, 6-(2-hydroxy-6-methoxyfurfurylamino)-9-β-D-2'-deoxyribofuranosylpurine, 6-(3-hydroxy-2-methoxyfurfurylamino)-9-β-D-2'-deoxyribofuranosylpurine, 6-(3-hydroxy-4-methoxyfurfurylamino)-9-β-D-2'-deoxyribofuranosylpurine, 6-(3-hydroxy-5-methoxyfurfurylamino)-9-β-D-2'-deoxyribofuranosylpurine, 6-(3-hydroxy-6-methoxyfurfurylamino)-9-β-D-2'-deoxyribofuranosylpurine, 6-(4-hydroxy-2-methoxyfurfurylamino)-9-β-D-2'-deoxyribofuranosylpurine, 6-(4-hydroxy-3-methoxyfurfurylamino)-9-β-D-2'-deoxyribofuranosylpurine, 6-(4-hydroxy-5-methoxyfurfurylamino)-9-β-D-2'-deoxyribofuranosylpurine, 6-(4-hydroxy-6-methoxyfurfurylamino)-9-β-D-2'-deoxyribofuranosylpurine, 6-(2-fluorobenzylamino)-9-β-D-2'-deoxyribofuranosylpurine, 6-(3-fluorobenzylamino)-9-β-D-2'-deoxyribofuranosylpurine, 6-(4-fluorobenzylamino)-9-β-D-2'-deoxyribofuranosylpurine, 6-(2-bromobenzylamino)-9-β-D-2'-deoxyribofuranosylpurine, 6-(3-bromobenzylamino)-9-β-D-2'-deoxyribofuranosylpurine, 6-(4-bromobenzylamino)-9-β-D-2'-deoxyribofuranosylpurine, 6-(2-iodobenzylamino)-9-β-D-2'-deoxyribofuranosylpurine, 6-(3-iodobenzylamino)-9-β-D-2'-deoxyribofuranosylpurine, 6-(4-iodobenzylamino)-9-β-D-2'-deoxyribofuranosylpurine, 6-(2-chlorobenzylamino)-9-β-D-2'-deoxyribofuranosylpurine, 6-(2-chlorobenzylamino)-9-β-D-2'-deoxyribofuranosylpurine, 6-(3-chlorobenzylamino)-9-β-D-2'-deoxyribofuranosylpurine, 6-(4-chlorobenzylamino)-9-β-D-2'-deoxyribofuranosylpurine, 6-(2-aminobenzylamino)-9-β-D-2'-deoxyribofuranosylpurine, 6-(3-aminobenzylamino)-9-β-D-2'-deoxyribofuranosylpurine, 6-(4-aminobenzylamino)-9-β-D-2'-deoxyribofuranosylpurine, 6-(2-methoxybenzylamino)-9-β-D-2'-deoxyribofuranosylpurine, 6-(3-methoxybenzylamino)-9-β-D-2'-deoxyribofuranosylpurine, 6-(4-methoxybenzylamino)-9-β-D-2'-deoxyribofuranosylpurine, 6-(2-hydroxybenzylamino)-9-β-D-2'-deoxyribofuranosylpurine, 6-(3-hydroxybenzylamino)-9-β-D-2'-deoxyribofuranosylpurine, 6-(4-hydroxybenzylamino)-9-β-D-2'-deoxyribofuranosylpurine, 6-(3,4-dihydroxybenzylamino)-9-β-D-2'-deoxyribofuranosylpurine, 6-(3,5-dihydroxybenzylamino)-9-β-D-2'-deoxyribofuranosylpurine, 6-(3,4-dihydroxybenzylamino)-9-β-D-2'-deoxyribofuranosylpurine, 6-(2,4-dihydroxybenzylamino)-9-β-D-2'-deoxyribofuranosylpurine, 6-(2,5-dihydroxybenzylamino)-9-β-D-2'-deoxyribofuranosylpurine, 6-(2,6-dihydroxybenzylamino)-9-β-D-2'-deoxyribofuranosylpurine, 6-(3,4-dimethoxybenzylamino)-9-β-D-2'-deoxyribofuranosylpurine, 6-(3,4-dimethoxybenzylamino)-9-β-D-2'-deoxyribofuranosylpurine, 6-(3,5-dimethoxybenzylamino)-9-β-D-2'-deoxyribofuranosylpurine, 6-(2,3-dimethoxybenzylamino)-9-β-D-2'-deoxyribofuranosylpurine, 6-(2,4-dimethoxybenzylamino)-9-β-D-2'-deoxyribofuranosylpurine, 6-(2,5-dimethoxybenzylamino)-9-β-D-2'-deoxyribofuranosylpurine, 6-(2,6-dimethoxybenzylamino)-9-β-D-2'-deoxyribofuranosylpurine, 6-(2-hydroxy-3-methoxybenzylamino)-9-β-D-2'-deoxyribofuranosylpurine, 6-(2-hydroxy-4-methoxybenzylamino)-9-β-D-2'-deoxyribofuranosylpurine, 6-(2-hydroxy-5-methoxybenzylamino)-9-β-D-2'-deoxyribofuranosylpurine, 6-(2-hydroxy-6-methoxybenzylamino)-9-β-D-2'-deoxyribofuranosylpurine, 6-(3-hydroxy-2-methoxybenzylamino)-9-β-D-2'-deoxyribofuranosylpurine, 6-(3-hydroxy-4-methoxybenzylamino)-9-β-D-2'-deoxyribofuranosylpurine, 6-(3-hydroxy-5-methoxybenzylamino)-9-β-D-2'-deoxyribofuranosylpurine, 6-(3-hydroxy-6-methoxybenzylamino)-9-β-D-2'-deoxyribofuranosylpurine, 6-(4-hydroxy-2-methoxybenzylamino)-9-β-D-2'-deoxyribofuranosylpurine, 6-(4-hydroxy-3-methoxybenzylamino)-9-β-D-2'-deoxyribofuranosylpurine, 6-(4-hydroxy-5-methoxybenzylamino)-9-β-D-2'-deoxyribofuranosylpurine, 6-(4-hydroxy-6-methoxybenzylamino)-9-β-D-2'-deoxyribofuranosylpurine.

Object of the invention are further compositions for inhibiting aging and/or for UV photoprotection of mammals, or for inhibiting aging and/or for UV photoprotection of mammalian cells, such as keratinocytes and fibroblasts, containing at least one 6-aryl-9-glycosidpurine of general formula I.

Object of the invention are also 6-aryl-9-glycosidpurines of general formula Ia

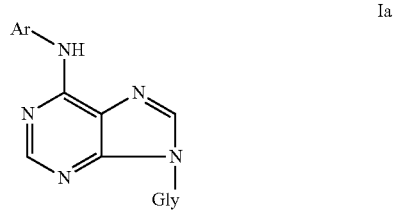

and pharmaceutically acceptable salts thereof with alkali metals, ammonia, amines, or addition salts with acids, wherein Gly represents β-D-arabinofuranosyl or β-D-2'-deoxyribofuranosyl, Ar represents benzyl or furfuryl, each of which is substituted by one or more, preferably one to three, substituents selected from the group comprising hydroxyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, or Ar is unsubstituted furfuryl, whereas, if Gly is β-D-arabinofuranosyl, Ar is not methyl-substituted benzyl.

The invention further encompasses cosmetic and/or tissue compositions containing as an active ingredient at least one compound of general formula Ia. Tissue compositions are especially suitable for use in biotechnologies.

Compositions

Suitable administration for cosmetic application is local, topical. The cosmetic composition typically contains from 0.1 to 95 wt. % of the active ingredient, whereas single-dose forms contain preferably 10 to 90 wt. % of the active ingredient and administration forms which are not single-dose preferably comprise 1 wt. % to 10 wt. % of the active ingredient. The application forms include, e.g., ointments, creams, pastes, foams, tinctures, lipsticks, drops, sprays, dispersions and the like. The compositions are prepared in a known manner, for example by means of conventional mixing, dissolving or lyophilizing processes.

Solutions of the active ingredients, suspensions or dispersions, especially isotonic aqueous solutions, dispersions and suspensions, can be prepared before use, for example in the case of lyophilised compositions which comprise the active substance alone or together with a carrier, for example mannitol.

Suspensions in oil comprise, as the oily component, vegetable, synthetic or semi-synthetic oils. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, erucic acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and composed of glycerides and polyethylene glycol esters; from Gattefoseé, Paris), "Labrasol" (saturated polyglycolated glycerides prepared by an alcoholysis of TCM and composed of glycerides and polyethylene glycol esters; from Gattefoseé, Paris) and/or "Miglyol 812" (triglyceride of saturated fatty acids of chain length $C_8$ to $C_{12}$ from Hills A G, Germany), and in particular vegetable oils, such as cottonseed oil, almond oil, olive oil, castor oil, sesame oil, soybean oil and, in particular, groundnut oil.

Ointments are oil-in-water emulsions which comprise not more than 70%, preferably 20 to 50% of water or aqueous phase. The fatty phase consists, in particular, of hydrocarbons, for example vaseline, paraffin oil or hard paraffins, which preferably comprise suitable hydroxy compounds, such as fatty alcohols or esters thereof, for example cetyl alcohol, or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances. Fatty ointments are non-aqueous and are in particular hydrocarbon-based, e.g. paraffin, vaseline or paraffin oil, and natural or semi-synthetic lipids, such as hydrogenated coconut fatty acid triglycerides or hydrogenated oils, such as hydrogenated castor or groundnut oil, and partially fatty acid glycerol esters, e.g. glycerol mono- and distearate. They further contain, e.g., fatty alcohols, emulsifiers and additives mentioned above in connection with ointments which increase water binding.

Creams are oil-in-water emulsions containing more than 50% of water. The oil bases used include fatty alcohols, e.g., isopropyl myristate, lanolin, bees wax or hydrocarbons, preferably vaseline (petrolatum) and paraffine oil. Emulsifiers are surface active compounds with predominantly hydrophilic characteristics, such as corresponding non-ionic emulsifiers, e.g., fatty acid polyalcohol esters or ethyleneoxy adducts thereof, e.g., polyglyceridic fatty acids or polyethylene sorbitan esters or acidic polyflyceridic fatty acid esters (Tween), polyoxyethylene fatty acid ethers or polyoxyethylene fatty acid esters; or corresponding ionic emulsifiers, such as alkali sulfate salts of fatty alcohols, such as sodium laurylsulfate, sodium cetylsulfate, or sodium stearylsulfate, which are typically used in the presence of fatty alcohols, e.g., cetyl stearyl alcohol or stearyl alcohol. The aqueous phase additives include agents preventing drying out of the creams, e.g., polyalcohols such as glycerol, sorbitol, propylene glycol and polyethylene glycol, and preservatives and fragrances.

Pastes are creams or ointments containing powdered secretion-absorbing components such as metal oxides, e.g., titanium oxides or zinc oxide, further talc or aluminium silicates for binding humidity or secretion.

Foams are applied from pressurized containers and include liquid oil-in-water emulsions in aerosol form, whereas the propellant gases include halogenated hydrocarbons such as chloro-fluoro-lower alkanes, e.g., dichlorofluoromethane and dichlorotetrafluoroethane, or preferably non-halogenated gaseous hydrocarbons, air, $N_2O$ or carbon dioxide. The oily phases used are the same as for ointments and the additives mentioned for ointments are used.

Tinctures and solutions usually comprise an aqueous-ethanolic base, to which humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The invention is further illustrated by the following examples which should not be construed as further limiting.

EXAMPLES OF CARRYING OUT THE INVENTION

Figure 1:
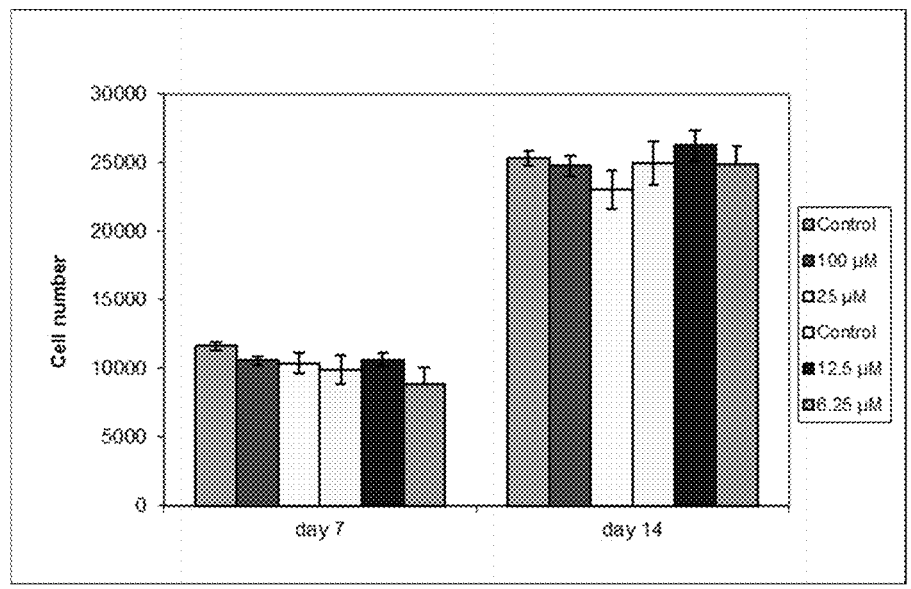
FIG. 1: Growth curve for the compound 6-benzylamino-9-β-D-arabinofuranosylpurine (Example 15).
Figure 2:
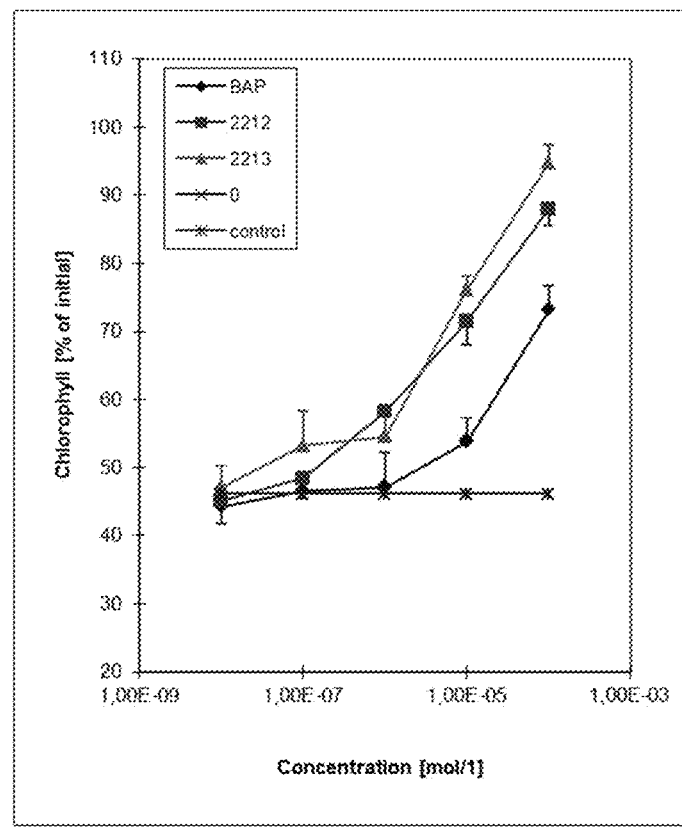
FIG. 2: Effect of 6-furfurylamino-9-β-D-arabinofuranosylpurine (2212) and 3-fluorobenzylamino-9-β-D-arabinofuranosylpurine (2213) on the retention of chlorophyl in extirpated wheat leaf segments (Example 18).

Example 1: Synthesis of 6-(3-methoxybenzylamino)-9-β-D-arabinofuranosylpurine 9-(β-D-arabinofuranosyl) hypoxantine (100 mg, 0.37 mmol), (benzotriazol-1-yloxy)tris(dimethylamino)phosphonium hexafluorophosphate (BOP, 196 mg, 0.44 mmol) and N,N-diisopropylethylamine (DIPEA, 97 µl, 0.56 mmol) were mixed in dimethylformamide (DMF, 1.86 ml). Subsequently, 3-methoxybenzylamine (56 µl, 0.56 mmol) was added. 9-(β-D-arabinofuranosyl) hypoxantine is commercially available (Jena Bioscience, N-1002) or can be prepared from 9-(β-D-arabinofuranosyl) adenine. Reaction mixture was mixed at laboratory temperature (25° C.) under argon overnight (16 hrs). After that period, reaction mixture was evaporated on vacuum rotary evaporator and one of the following procedures was used to obtain the crude product: First, the reaction mixture was purified by column liquid chromatography (mobile phase chloroform-methanol 19:1) or cold water was slowly added (15 ml) and the reaction mixture was vortexed: a yellowish substance started to occur after a few minutes. Reaction mixture was than placed into the fridge and left overnight. Arising product was filtrated and once recrystallized from isopropanol and twice from ethanol. Final product is a white crystalline solid. Both ways of isolation of the product described above gave 40% yield, TLC (40% chlorform:metanol (90:10, v:v): one spot; HPLC purity >98%. [M+H$^+$]388, $^1$H (DMSO-d$_6$, 300 MHz) δ ppm: 3.65-3.66 (m, 2H), 3.70 (s, 3H), 3.78 (d, J=3.7 Hz), 4.14 (s, 2H), 4.67 (bs, 2H), 5.09 (t, J=5.3 Hz), 5.52 (d, J=3.8 Hz), 5.61 (d, J=4.5 Hz), 6.27 (d, J=3.9 Hz), 6.77 (d, J=7.1 Hz), 6.89 (s, 1H), 6.91 (s, 1H), 7.20 (t, J=7.6 Hz), 8.19 (s, 1H), 8.21 (s, 1H), 8.34 (bs, 1H).

Example 2: Synthesis of 6-(3-hydroxybenzylamino)-9-β-D-arabinofuranosylpurine 9-(β-D-arabinofuranosyl) hypoxantine (100 mg, 0.37 mmol), BOP (196 mg, 0.44 mmol) and DIPEA (97 µl, 0.56 mmol) were mixed in v DMF (1.86 ml). Subsequently, 3-hydroxybenzylamine (50 µl, 0.50 mmol) was added. 9-(β-D-arabinofuranosyl) hypoxantine is commercially available (Jena Bioscience, N-1002). Reaction mixture was mixed under argon atmosphere at laboratory temperature (25° C.) overnight (10 hrs). Reaction mixture was evaporated using vacuum rotary evaporator and purified by column liquid chromatography (mobile phase chloroform:methanol 19/1). Product is a white crystalline solid, yield 5%, TLC (chlorform:metanol (90:10, v:v): one spot; HPLC purity >98%, [M+H$^+$]374, NMR: $^1$H (DMSO-d$_6$, 300 MHz) β ppm: 3.66 (s, 2H), 3.78 (s, 1H), 4.15 (s, 2H), 4.63 (bs 2H), 5.12 (s, 1H), 5.55 (s, 1H), 5.64 (s, 1H), 6.28 (s, 1H), 6.58 (d, J=7.5 Hz), 6.73 (s, 1H), 6.76 (s, 1H), 7.07 (t, J=7.5 Hz), 8.19 (s, 1H), 8.21 (s, 1H), 9.27 (bs, 1H).

Example 3: Synthesis of 6-(3-fluorobenzylamino)-9-β-D-arabinofuranosylpurine 9-(β-D-arabinofuranosyl) hypoxantine (100 mg, 0.37 mmol), BOP (196 mg, 0.44 mmol) and DIPEA (97 µl, 0.56 mmol) were mixed together in DMF (1.86 ml) and subsequently, 3-fluorbenzylamine (70 µl, 0.76 mmol) was added. 9-(β-D-arabinofuranosyl) hypoxantine was prepared from commercially available 9-(β-D-arabinofuranosyl)adenine. Reaction mixture was mixed under argon at laboratory temperature of 25° C. for 24 h. Reaction mixture was evaporated on vacuum rotary evaporator and cold water was added after small portions of 15 ml. After several minutes of vortexing, yellowish substance started to occur. Reaction mixture was then refridgerated for 10 hrs. A product was filtered off and once recrystallized using isopropanol and twice using ethanol. Produkt is a white crystalline solid, in both cases of isolation, the yield 70%, TLC (chlorform: metanol (90:10, v:v): one spot; HPLC purity >98%. [M+H$^+$] 376, NMR: $^1$H (DMSO-d$_6$, 300 MHz) δ ppm: 3.66 (s, 2H), 3.79 (s, 1H), 4.14 (s, 2H), 4.74 (bs, 2H), 5.09 (s, 1H), 5.50 (s, 1H), 5.60 (s, 1H), 6.29 (s, 1H), 7.17 (s, 4H), 8.22 (s, 2H), 8.37 (bs, 1H).

Example 4: Synthesis of 6-(3-iodobenzylamino)-9-β-D-arabinofuranosylpurine 9-(β-D-arabinofuranosyl) hypoxantine (100 mg, 0.37 mmol), BOP (196 mg, 0.44 mmol) were mixed together in DMF (2 ml) and subsequently, 3-iodbenzylamine (60 µl) and DIPEA (97 µl) was added. 9-(β-D-arabinofuranosyl) hypoxantine was prepared from commercially available 9-(β-D-arabinofuranosyl)adenine. Reaction mixture was mixed under argon atmosphere in oil bath at the temperature of 60° C. for 24 h. Reaction mixture was evaporated on vacuum rotary evaporator. Arising gel was absorbed to silicagel and chromatography columns was used for sample purification using chloroform:methanol mobile phase with the gradient 99:1 to 9:1. TLC (chlorform:metanol (90:10, v:v): one spot; HPLC purity >98%. [M+H$^+$] 484, NMR: $^1$H (DMSO-d$_6$, 300 MHz) δ ppm: $^1$H (DMSO-d$_6$, 500 MHz) δ ppm: 3.6 (s, 1H), 3.7 (s, 1H), 3.76-3.81 (m, 2H), 4.09-4.17 (m, 2H), 4.64 (bs, 1H), 5.23 (bs, 1H), 5.66 (bs, 2H), 6.24 (d, J=5 Hz, 1H), 7.09 (t, J=7.5 Hz, 1H), 7.34 (d, J=7.5 Hz, 1H), 7.55 (d, J=8 Hz, 1H), 7.69 (s, 1H), 8.18 (s, 1H), 8.21 (s, 1H), 8.37 (bs, 1H)

Example 5: Synthesis of 6-furfurylamino-9-β-D-arabinofuranosylpurine 6-chloropurine tetraacetylarabinopyranoside (100 mg, 0.242 mmol) dispersed in methanol (3 ml) was placed into microwave reactor CEM SP reaction vessel (10 ml). Subsequently, furfurylamine (26.8 µl, 0.291 mmol) with triethylamine (151 µl, 1.09 mmol) were added. Reaction conditions were adjusted as follows: dynamic method, it means: reaction time 3 hrs, temperature: 100° C., pressure 100 psi and performance: 50 watt. Reaction mixture was evaporated using vacuum rotary evaporator and purified using column liquid chromatography (mobile phase: chloroform:methanol 9/1). The product is a white solid: kinetin arabinopyranoside, mixture of α and β anomers in ration 5/1. The anomers were separated from each other: yield: 30% of α anomer and 10% of β anomer. Starting compound 6-chloropurine tetraacetylarabinopyranoside was prepared as follows: 6-chloropurine (0.412 g, 2.66 mmol) was placed into a dry flask and a tetraacetylarabinose (0.771 g 2.42 mmol) dissolved in dry acetonitrile was added through the septum by a needle (15 ml). Subsequently, tin tetrachloride was slowly added by a needle (5.6 mmol 0.6 ml). Reaction mixture was mixed at laboratory temperature under argon overnight. After that period, a mixture was evaporated using vacuum evaporater and ethylacetate (25 ml) was added. Organic phase was extracted by sodium carbonate solution (30 ml) and water (2×30 ml) and after that dried over sodium sulphate and again evaporated using vacuum evaporator. A product was purified by column liquid chromatography, mobile dichlormethane-aceton 9/1. As the result after the evaporation of organic solvents, there occurred clear gel like residue and this residue was mixed with diethyl ether and changed into a white solid 6-chloropurine tetraacetylarabinopyranosid, a mixture of α and β anomers. Yield: 50%, HPLC purity: 98%, [M+H$^+$] 348, NMR: $^1$H (DMSO-d$_6$, 300 MHz) δ ppm: 3.61-3.72 (m, 2H), 3.78 (d, J=3.9 Hz), 4.14 (s, 2H), 4.69 (bs, 2H), 5.11 (t, J=5.4 Hz), 5.54 (d, J=3.9 Hz), 5.62 (d, J=4.8 Hz), 6.22 (d, J=2.7 Hz), 6.27 (d, J=4.2 Hz), 6.36 (t, J=3.0 Hz), 7.54 (s, 1H), 8.21 (s, 3H).

Example 6: Synthesis of 6-(2-chlorobenzylamino)-9-β-D-arabinofuranosylpurine 9-(β-D-arabinofuranosyl) hypoxantine (100 mg, 0.37 mmol), BOP (196 mg, 0.44 mmol) were mixed together in DMF (2 ml) and subsequently, 2-chlorobenzylamine (55 µl) and DIPEA (97 µl) was added. Reaction mixture was mixed under argon atmosphere in oil bath at the temperature of 60° C. for 24 h. Reaction mixture was evaporated on vacuum rotary evaporator. MeOH with a drop of chloroform was added to distillation residue and the mixture was ultrasonised. The process formed arising of a white paste solid that was filtrated. The resulted white solid was re-crystallized from EtOH and left in refridgerator overnight. Result was a white solid. TLC (chlorform:metanol (90:10, v:v): one spot; HPLC purity >98%. [M+H$^+$] 392, NMR: $^1$H (DMSO-d$_6$, 300 MHz) δ ppm: $^1$H (DMSO-d$_6$, 500 MHz) δ ppm: 3.60-3.71 (m, 2H), 3.77 (q, J=4 Hz, 1H), 4.11-4.15 (m, 2H), 4.69 (bs, 2H), 5.14 (bs, 1H), 5.57 (bs, 2H), 6.25 (d, J=4.5 Hz, 1H), 7.25-7.33 (m, 3H), 7.36 (s, 1H), 8.18 (s, 1H), 8.21 (s, 1H), 8.40 (bs, 1H).

Example 7: The synthesis of 6-(2-aminobenzylamino)-9-β-D-arabinofuranosylpurine 9-(β-D-arabinofuranosyl) hypoxantine (100 mg, 0.37 mmol), BOP (196 mg, 0.44 mmol) were mixed together in DMF (2 ml) and subsequently, 2-aminobenzylamine (55 µl) and DIPEA (97 µl) was added. Reaction mixture was mixed under argon atmosphere in oil bath at the temperature of 60° C. for 24 h. Reaction mixture was evaporated on vacuum rotary evaporator. The resulted distillation residue was re-crystallized from EtOH and left in refridgerator overnight. Result was a white solid that was filtrated off and dried. TLC (chlorform:metanol (90:10, v:v): one spot; HPLC purity >98%, NMR: $^1$H (DMSO-d$_6$, 300 MHz) δ ppm: $^1$H (DMSO-d$_6$, 500 MHz) δ ppm: 3.59-3.70 (m, 2H), 3.77 (q, J=4 Hz, 1H), 4.11-4.15 (m, 2H), 4.51 (bs, 2H), 5.10 (t, J=5.5 Hz, 1H), 5.20 (s, 2H), 5.52 (d, J=4 Hz, 1H), 5.60 (d, J=5 Hz, 1H), 6.26 (d, J=4 hz, 1H), 6.46 (0=7.5 Hz, 1H), 6.59 (d, J=8 Hz, 1H), 6.91 (t, J=7.5 Hz, 1H), 7.07 (d, J=7.5 Hz, 1H), 8.19 (s, 3H)

TABLE 1

6-substituted-9-β-D-arabinofuranosylpurines prepared by the method according to Examples 1-7, elemental analyses and ES-MS measurement results of these compounds

| Substituent in position 6 (—NH—Ar) | Elemental analysis calculated/found | | | ES-MS [M + H$^+$] |
|---|---|---|---|---|
| | % C | % H | % N | |
| furfurylamino | 51.9/51.6 | 4.9/4.8 | 20.2/20.2 | 348 |
| 2-fluorobenzylamino | 54.4/54.1 | 4.8/4.8 | 18.7/18.4 | 376 |
| 3-fluorobenzylamino | 54.4/53.9 | 4.8/4.7 | 18.7/18.2 | 376 |
| 4-fluorobenzylamino | 54.4/54.3 | 4.8/4.8 | 18.7/18.3 | 376 |
| 2-chlorobenzylamino | 52.1/52.0 | 4.6/4.7 | 17.9/17.5 | 392 |
| 3-chlorobenzylamino | 52.1/51.9 | 4.6/4.6 | 17.9/17.3 | 392 |
| 4-chlorobenzylamino | 52.1/51.8 | 4.6/4.5 | 17.9/17.1 | 392 |
| 2-bromobenzylamino | 46.8/46.3 | 4.2/4.1 | 16.1/15.5 | 437 |
| 3-bromobenzylamino | 46.8/47.8 | 4.2/4.5 | 16.1/15.6 | 437 |
| 4-bromobenzylamino | 46.8/46.9 | 4.2/4.3 | 16.1/15.4 | 437 |
| 3-iodobenzylamino | 42.3/42.4 | 3.8/3.9 | 14.5/14.6 | 484 |
| 2-methoxybenzylamino | 55.8/55.9 | 5.5/5.3 | 18.1/17.9 | 388 |
| 3-methoxybenzylamino | 55.8/55.5 | 5.5/5.7 | 18.1/18.0 | 388 |
| 4-methoxybenzylamino | 55.8/55.6 | 5.5/5.5 | 18.1/18.1 | 388 |

TABLE 1-continued 6-substituted-9-β-D-arabinofuranosylpurines prepared
by the method according to Examples 1-7, elemental analyses
and ES-MS measurement results of these compounds

| Substituent in position 6 (—NH—Ar) | Elemental analysis calculated/found | | | ES-MS [M + H⁺] |
|---|---|---|---|---|
| | % C | % H | % N | |
| 2-hydroxybenzylamino | 54.7/54.6 | 5.1/5.0 | 18.8/18.8 | 374 |
| 3-hydroxybenzylamino | 54.7/54.5 | 5.1/5.1 | 18.8/18.5 | 374 |
| 4-hydroxybenzylamino | 54.7/54.6 | 5.1/4.9 | 18.8/18.6 | 374 |
| 2,4-dichlorobenzylamino | 47.9/47.8 | 4.0/4.1 | 16.4/16.5 | 427 |
| 3,4-dichlorobenzylamino | 47.9/47.9 | 4.0/4.2 | 16.4/16.5 | 427 |
| 2,3-dihydroxybenzylamino | 52.4/52.5 | 4.9/4.8 | 18.0/18.1 | 390 |
| 3,5-dihydroxybenzylamino | 52.4/52.6 | 4.9/4.9 | 18.0/18.3 | 390 |
| 2-hydroxy-3-methoxybenzylamino | 53.6/53.4 | 5.2/5.1 | 17.4/17.5 | 404 |
| 3-hydroxy-4-methoxybenzylamino | 53.6/53.5 | 5.2/5.0 | 17.4/17.6 | 404 |
| 2,3-dimethoxybenzylamino | 54.7/54.8 | 5.6/5.7 | 16.8/16.7 | 418 |
| 2,4-dimethoxybenzylamino | 54.7/54.6 | 5.6/5.5 | 16.8/16.6 | 418 |
| 3,4-dimethoxybenzylamino | 54.7/54.8 | 5.6/5.6 | 16.8/16.5 | 418 |
| 3,5-dimethoxybenzylamino | 54.7/54.6 | 5.6/5.7 | 16.8/16.9 | 418 |

Example 8: The synthesis of 6-(3-methoxybenzy-lamino)-9-β-D-arabinofuranosylpurine in Bench Scale Feedstock: 9-β-D-Arabinofuranosyl-hypoxanthine (1072 g, 4 mol),
(Benzotriazol-1-yloxy)tris(dimethylamino)phosphonium hexafluorophosphate (BOP, 2124 g (4.8 mol), dimethylformamide (DMF, 20 L, N,N-Diisopropyl-N-ethylamine (DIPEA, 1045 mL (6 mol), 3-methoxybenzylamine (658 g, 4.8 mol), demi water 40 l, 2-propanol 30 L.

Procedure:
Dimethylformamide (20 l) was placed into a glass duplicated reactor A1 equiped with thermometer (PT100) and reflux condenser. Reactor was filled in with inert atmosphere (nitrogen). Stirring with hopper opening was switched on. 9-β-D-arabinattranosyl hypoxanthine and BOP (2124 g) were poured to the reactor using the respirator. As soon as the solid is dissolved, DIPEA (1045 mL) and 3-methoxybenzylamine (658 g) were added. The reactor stayed under continuous mild nitrogen flow. Reaction mixture was heated (using duplication) to 50° C., and was stirred for 20 hrs. Reaction course control: after 12 hrs of reaction, sample for TLC: 1 ml aliquot was dilluted by 4 ml of methanol and the solution was applied next to the other starting compounds and standard product on TLC plate. TLC plate was evolved in the following mobile phase: chloroform:methanol:ammonium water solution; 4:1:0.05). If the reaction was still not finished, the mixture was further stirred at 50° C., but next portion of BOP could be also added (200 g). If the reaction was finished (>90%), reaction mixture was cooled (via duplication) to the temperature of 20-25° C. and after that was reaction mixture drained into the transport vessel. Reactor was subsequently splashed with a small amount of methanol (3×1 L), and methanolic portions were mixed with reaction mixture). Reaction mixture was evaporated on rotary evaporator—a vacuum was secured by water ring vacuum pump parameters such as pressure and temperature were established according to technolog instructions. Distillation residue was (hot) drained into transport vessel. Evaporator was splashed with hot methanol and this portion was evaporated using vacuum evaporater separately from the main portion. Reactor A1 was filled with demi water (40 L), stirring and cooling in duplication was switched on. Reactor was cooled to 10° C. and distillation residue was slowly added. Transport vessel was splashed with methanol (3×250 mL) and methanolic solution was also poured into the reactor. The reactor content was stirred for three hours at 10-15° C. Emerging precipitate was filtered off on great Büchner channel and washed first with cold water (+5° C.) than only by water (4×1 L). Crude product was dried in a convection oven at 80° C. Yield: 1200-1250 g.

Crystallization of 6-(3-methoxybenzylamino)-9-β-D-arabinofuranosylpurine

Crude product: 1000 g, 2-propanol: 18 l, active carbon CXV 50 g
Procedure: 2-propanol (15 l) was poured into A1 reactor and stirring was switched on.
Crude 6-(3-methoxybenzylamino)-9-β-D-arabinofuranosylpurin (1000 g) was added. The content or reactor was heated via duplication to 80° C. the solid of crude product should be dissolved. If the product was not dissolved, it is necessary to continue stirring at 80° C., or add next portion of 2-propanol. As soon as was all solid dissolved, active carbon was added and stirring is continued at 80° C. for 15 minutes. After that, the solution was filtrated off using preheated Büchner channel (preheated in convection oven, 110° C.). Glass reactor was rinsed by 2-propanol (2×1 L) and filtration cake was washed with this portion of 2-propanol Búchner chanell. Filtrate and flushing were merged together and placed into transport vessel for crystallization. Product crystallized at the temperature of +5-+10° C. for 12 hrs. After the solid appeared, the product was filtrated off, rinsed with cold (+5° C.) 2-propanol (3×500 mL) and dried in convection oven at 70° C. to constant weight. Yield: 750-800 g, HPLC purity: >98%.

Example 9: Synthesis of 6-(3-methoxybenzylamino)-9-β-D-2'-deoxyribofuranosylpurine 2'-deoxyinosine (252 mg) and BOP (531 mg) were dissolved in dry DMF (5 ml) and stirred at laboratory temperature under argon atmosphere. After five minutes, DIPEA (261 µl) and 3-methoxybenzylamine (167 µl) were added. Reaction mixture was stirred at laboratory temperature for 16 hrs. Reaction process was controlled via TLC (mobile phase: chloroform-methanol-25% aqueous ammonia, 4:1: 0.05). As soon as the conversion was not complete, next portion BOP (354 mg; 0.8 mmol) was added and reaction mixture was heated to 60° C. and stirred for 6 hrs. As soon as there were not detected a spot of starting 2'-deoxyinosine, reaction mixture was evaporated using vacuum evaporator (maximal temperature 55° C.). A residue (cca 1.5 g) was chromatographically purified using silica gel (150 g); mobile phase: 0-20% methanol in dichlormethane. Yield: 270 mg (79%), HPLC-MS purity: 98+%, [M+H⁺] 372, mp 165-170° C., C/H/N: 58.2/58.1; 5.7/5.7; 18.9/18.8; ¹H (DMSO-d₆, 300 MHz) δ ppm: 2.25-2.37 (m, 1H), 2.45-2.64 (m, 1H), 3.50-3.68 (m, 2H), 3.70 (s, 3H), 3.85-3.90 (m, 1H), 4.33-4.45 (m, 1H), 4.67 (bs, 2H), 4.85 (t, 1H), 5.10 (d, J=4.0 Hz), 6.30 (t, J=6.9 Hz), 6.77 (d, J=7.1 Hz), 6.89 (s, 1H), 6.91 (s, 1H), 7.20 (t, J=7.6 Hz), 8.19 (s, 1H), 8.21 (s, 1H), 8.34 (bs, 1H).

Example 10: Synthesis of 6-(2-hydroxybenzylamino)-9-β-D-2'-deoxyribofuranosylpurine 2'-deoxyinosine (252 mg) and BOP (664 mg) were dissolved in dry DMF (8 ml) and stirred at laboratory temperature under argon atmosphere. After five minutes, DIPEA (348 μl) and 2-hydroxybenzylamine (131 μl) were added. Reaction mixture was stirred at 50° C. for 20 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 60° C. and stirred for 10 hrs. As soon as there were not detected a spot of starting 2'-deoxyinosine, reaction mixture was evaporated using vacuum evaporator (maximal temperature 55° C.). A residue (cca 1.5 g) was chromatographically purified using silica gel (150 g); mobile phase: 0-20% methanol in dichlormethane. Yield: 250 mg (70%), HPLC-MS purity: 98+%, [M+H$^+$] 358, mp 172-175° C., C/H/N: 57.1/57.2; 5.3/5.4; 19.6/19.2; $^1$H (DMSO-d$_6$, 300 MHz) δ ppm: 3.66 (s, 2H), 3.78 (s, 1H), 4.15 (s, 2H), 4.63 (bs 2H), 5.12 (s, 1H), 5.55 (s, 1H), 5.64 (s, 1H), 6.28 (s, 1H), 6.58 (d, J=7.5 Hz), 6.73 (s, 1H), 6.76 (s, 1H), 7.07 (t, J=7.5 Hz), 8.19 (s, 1H), 8.21 (s, 1H), 9.27 (bs, 1H).

Example 11: Synthesis of 6-(2-hydroxy-3-methoxy-benzylamino)-9-β-D-2'-deoxyribofuranosylpurine 2'-deoxyinosine (252 mg) and BOP (664 mg) were dissolved in dry DMF (10 ml) and stirred at 50° C. After five minutes, DIPEA (348 μl) and 2-hydroxy-3-methoxybenzylamine (165 μl) were added. Reaction mixture was stirred at laboratory temperature for at least 20 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 70° C. and stirred for 6 hrs. As soon as there were not detected a spot of starting 2'-deoxyinosine, reaction mixture was evaporated using vacuum evaporator (maximal temperature 55° C.). A residue (cca 1.5 g) was chromatographically purified using silicagel (150 g); mobile phase: 0-20% methanol in dichlormethane. Yield: 270 mg (79%), HPLC-MS purity: 98+%, mp 174-178° C., [M+H$^+$]0 388, C/H/N: 55.8/55.3; 5.5/5.6; 18.1/18.2; $^1$H (DMSO-d$_6$, 300 MHz) δ ppm: 2.25-2.37 (m, 1H), 2.45-2.64 (m, 1H), 3.50-3.68 (m, 2H), 3.77 (s, 3H), 3.85-3.90 (m, 1H), 4.33-4.45 (m, 1H), 4.67 (bs, 2H), 4.85 (t, 1H), 5.10 (d, J=4.0 Hz), 5.39 (d, J=6.0 Hz), 6.30 (t, J=6.9 Hz), 6.77 (d, J=7.1 Hz), 6.89 (s, 1H), 7.20 (t, J=7.6 Hz), 8.19 (s, 1H), 8.21 (s, 1H), 8.34 (bs, 1H).

Example 12: Synthesis of 6-(furfurylamino)-9-β-D-2'-deoxyribofuranosylpurine 2'-deoxyinosine (252 mg) and BOP (670 mg) were dissolved in dry DMF (10 ml) and stirred at laboratory temperature under argon atmosphere. After five minutes, DIPEA (350 μl) and furfurylamine (150 μl) were added. Reaction mixture was stirred at 60° C. for at least 10 hrs. Reaction process was controlled via TLC (mobile phase: chloroform-methanol-25% aqueous ammonia, 4:1:0.05). As soon as the conversion was not complete, next portion BOP (354 mg; 0.8 mmol) was added and reaction mixture was heated to 70° C. and stirred for 6 hrs. As soon as there were not detected a spot of starting 2'-deoxyinosine, reaction mixture was evaporated using vacuum evaporator (maximal temperature 55° C.). A residue (cca 1.5 g) was chromatographically purified using silica gel (150 g); mobile phase: 0-20% methanol in dichlormethane. Yield: 300 mg (82%), HPLC-MS purity: 98+%, [M+H$^+$] 332, C/H/N: 54.4/54.3; 5.2/5.2; 19.3/19.5$^1$H (DMSO-d$_6$, 300 MHz) δ ppm: 3.61-3.72 (m, 2H), 3.78 (d, J=3.9 Hz), 4.14 (s, 2H), 4.69 (bs, 2H), 5.11 (t, J=5.4 Hz), 5.54 (d, J=3.9 Hz), 5.62 (d, J=4.8 Hz), 6.22 (d, J=2.7 Hz), 6.27 (d, J=4.2 Hz), 6.36 (t, J=3.0 Hz), 7.54 (s, 1H), 8.21 (s, 3H).

TABLE 2

6-substituted-9-β-D-2'-deoxyribofuranosylpurines prepared according to examples 9-12

| Substituent in position 6 (—NH—Ar) | Elemental analysis calculated/found | | | ES-MS [M + H$^+$] |
|---|---|---|---|---|
| | % C | % H | % N | |
| 4-methylfurfurylamino | 55.6/55.5 | 5.5/5.6 | 18.5/18.4 | 346 |
| 5-methylfurfurylamino | 55.6/55.4 | 5.5/5.6 | 18.5/18.3 | 346 |
| 4-hydroxyfurfurylamino | 51.9/51.8 | 4.9/5.0 | 20.2/20.1 | 348 |
| 5-hydroxyfurfurylamino | 51.9/52.0 | 4.9/4.8 | 20.2/20.2 | 348 |
| 3-chlorobenzylamino | 54.3/54.2 | 4.8/4.8 | 18.6/18.6 | 376 |
| 4-chlorobenzylamino | 54.3/54.3 | 4.8/4.9 | 18.6/18.5 | 376 |
| 2-bromobenzylamino | 48.6/48.7 | 4.3/4.4 | 16.7/16.7 | 421 |
| 3-bromobenzylamino | 48.6/48.6 | 4.3/4.5 | 16.7/16.8 | 421 |
| 4-bromobenzylamino | 48.6/48.3 | 4.3/4.3 | 16.7/16.9 | 421 |
| 2-methoxybenzylamino | 58.2/58.3 | 5.7/5.5 | 18.9/18.6 | 372 |
| 3-methoxybenzylamino | 58.2/58.1 | 5.7/5.9 | 18.9/18.7 | 372 |
| 2-hydroxybenzylamino | 57.1/57.2 | 5.4/5.3 | 19.6/19.8 | 358 |
| 3-hydroxybenzylamino | 57.1/57.3 | 5.4/5.3 | 19.6/19.5 | 358 |
| 4-hydroxybenzylamino | 57.1/57.1 | 5.4/5.2 | 19.6/19.5 | 358 |
| 2,3-dihydroxybenzylamino | 54.7/54.5 | 5.1/5.2 | 18.8/18.7 | 374 |
| 3,5-dihydroxybenzylamino | 54.7/54.8 | 5.1/5.3 | 18.8/18.6 | 374 |
| 2-hydroxy-3-methoxybenzylamino | 55.8/55.7 | 5.5/5.6 | 18.1/18.2 | 388 |
| 3-hydroxy-4-methoxybenzylamino | 55.8/55.6 | 5.5/5.7 | 18.1/18.3 | 388 |
| 2,3-dimethoxybenzylamino | 56.9/56.8 | 5.8/5.7 | 17.5/17.4 | 402 |
| 2,4-dimethoxybenzylamino | 56.9/56.9 | 5.8/5.6 | 17.5/17.5 | 402 |
| 3,4-dimethoxybenzylamino | 56.9/56.8 | 5.8/5.9 | 17.5/17.7 | 402 |
| 3,5-dimethoxybenzylamino | 56.9/56.9 | 5.8/5.9 | 17.5/17.8 | 402 |

Example 13: Evaluation of Cytotoxicity of Novel Derivatives for Skin Cell by MTT in Vitro Test MTT assay is a standard test of toxicity based on photometric measurement of the ability of metabolically active cells to reduce MTT (3-(4,5-dimethylthiazol-2-yl)-2,5-diphenyltetrazolium bromide). Using the assay, the effects of 72 hour treatments with several concentrations of the compounds (sixfold dilution, maximal concentration=50 microM) on viability of skin fibroblasts BJ and keratinocytes HaCaT were evaluated. About 5,000 cells were seeded per well of a 96-well plate 24 hours before the treatment. DMSO vehiculum was used as a negative control. After 72 hour treatment, new medium with MTT (Sigma, M2128) was added to a final concentration of 0.5 mg/ml. After 3 hours, medium was removed and resulting formazan in the cells was dissolved in DMSO. The absorbance was measured at 570 nm (640 nm reference wavelength). The IC50 values were calculated from the dose-response curves. 6-Benzylaminopurine riboside and 6-furfurylaminopurine riboside were used as positive controls they were toxic in the MTT test. The following results were obtained.

| | IC50 (μM) |
|---|---|
| dimethylsulfoxide | >50 |
| 6-benzylamino-9-β-D-arabinofuranosylpurine | >50 |
| 6-furfurylamino-9-β-D-arabinofuranosylpurine | >50 |
| 6-(3-methoxybenzylamino)-9-β-D-arabinofuranosylpurine | >50 |
| 6-(2-chlorobenzylamino)-9-β-D-arabinofuranosylpurine | >50 |
| 6-(3-hydroxybenzylamino)-9-β-D-arabinofuranosylpurine | >50 |
| 6-(3-chlorobenzylamino)-9-β-D-arabinofuranosylpurine | >50 |

-continued

| | IC50 (µM) |
|---|---|
| 6-(2,3-dimethoxybenzylamino)-9-β-D-arabinofuranosylpurine | 49 |
| 6-(2,3,4-trimethoxybenzylamino)-9-β-D-arabinofuranosylpurine | 48 |
| 6-(3-iodobenzylamino)-9-β-D-arabinofuranosylpurine | >50 |
| 6-(3-aminobenzylamino)-9-β-D-arabinofuranosylpurine | >50 |
| 6-(furfurylamino)-9-β-D-2'-deoxyribofuranosylpurine | >50 |
| 6-(2-hydroxybenzylamino)-9-β-D-2'-deoxyribofuranosylpurine | >50 |
| 6-benzylaminopurin9-ribosylpurine (comparative example) | ≤3 |
| 6-furfurylamino-9-ribosylpurine (comparative example) | ≤3 |

Example 14: SRB In Vitro Toxicity Test

SRB (sulforhodamine B) assay is a standard toxicity test based on a photometric measurement of the cellular protein content after the staining with sulphorhodamine B. Using the assay, the effects of 72 hour treatments with several concentrations of the compounds (sixfold dilution, maximal concentration=50 microM) on viability of skin fibroblasts BJ and keratinocytes HaCaT were evaluated. About 5,000 cells were seeded per well of a 96-well plate 24 hours before the treatment. DMSO vehiculum was used as a negative non-toxic control. 6-benzylaminopurine riboside a 6-furfurylaminopurin riboside were used as positive toxic controls. After three days the medium was removed and the cells fixed with 10% (wt/vol) trichloroacetic acid. After the extensive washing in distilled water, 0.4% (wt/vol) solution of SRB in acetic acid was added and the fixed cells were stained for 30 minutes. The unbound stain was washed away by distilled water and the bound SRB was solubilized in unbuffered 10 mM Tris base. Absorbance was measured at 564 nm. IC50 values were calculated from dose-response curves.

The following results were obtained:

| | IC 50 (µM) |
|---|---|
| dimethylsulfoxide | >50 |
| 6-benzylaminopurine-9-β-D-arabinofuranosylpurine | >50 |
| 6-furfurylamino-9-β-D-arabinofuranosylpurine | >50 |
| 6-(3-methoxybenzylamino)-9-β-D-arabinofuranosylpurine | >50 |
| 6-(2-chlorobenzylamino)-9-β-D-arabinofuranosylpurine | >50 |
| 6-(3-hydroxybenzylamino)-9-β-D-arabinofuranosylpurine | >50 |
| 6-(3-chlorobenzylamino)-9-β-D-arabinofuranosylpurine | 48 |
| 6-(3-iodobenzylamino)-9-β-D-arabinofuranosylpurine | >50 |
| 6-(3-aminobenzylamino)-9-β-D-arabinofuranosylpurine | >50 |
| 6-(furfurylamino)-9-β-D-2'-deoxyriboside | >50 |
| 6-(2-hydroxybenzylamino)-9-β-D-2'-deoxyriboside | >50 |
| 6-(2,3-dimethoxybenzylamino)-9-β-D-arabinofuranosylpurine | >50 |
| 6-(2,3,4-trimethoxybenzylamino)-9-β-D-arabinofuranosylpurine | >50 |
| 6-furfurylamino-9-ribosylpurine (comparative example) | ≤3 |

Example 15: One-Step Growth Curve for the Compound 6-(benzylamino)purine-9-β-D-arabinofuranosylpurine The experiments were performed with BJ skin fibroblasts in 24-well tissue culture plates. About 10,000 cells in culture medium comprising DMEM with 10% FBS were seeded into the individual wells. The cells were allowed to attach for 24 hourse. The test compound was added to final concentrations in a range from 12.5 to 100 µM. DMSO vehiculum was also tested. In order to control for variability, two plate columns (A, D) were treated with DMSO vehiculum. The culture medium with the test chemicals or DMSO vehiculum was changed twice a week. Following trypsinization, the numbers of cells in 4 wells for each concentration were counted using Coulter counter on 7th and 14th day. The obtained results are showed in FIG. 1. The tested compound did not have a negative influence on cell viability.

Example 16: In Vitro Test of Skin Irritation in EpiDERM™

EpiDERM™ is a 3D model of epidermis manufactured by Mattek company. The effects of tested substances are evaluated by MTT. 2 solutions (2 application forms) of the compounds 6-furfurylamino-9-β-D-arabinofuranosylpurine and 6-(3-methoxybenzylamino)-9-β-D-arabinofuranosylpurine in concentrations 1 mM a 200 microM in 0.5% DMSO/99.5% PBS were evaluated according to a standard protocol "INVITRO EpiDerm™ SKIN IRRITATION TEST". After a preincubation of the tissues, 30 microliters of the application form solution were applied on the individual tissues. The exposition time was 60 minutes. Three tissues were used for each tested concentration as well as for controls. Following washing out of the applied solution, the tissues were incubated for 42 hour in order to allow a reparation of possible damage. In the next step, the tissue was incubated with MTT for 3 hours. The resulting formazan was extracted to iso-propanol. Relative viability of the individual tissues was calculated as a percentage of viability of the average of the negative controls. Average viability of the tissues treated with 1 mM solution of the test substance was 99.3% for the compound 6-(3-methoxybenzylamino)-9-β-D-arabinofuranosylpurine and 98.0% for the compound 6-(furfurylamino)-9-β-D-arabinofuranosylpurine where 100% is an average viability of the tissues treated with the solvent only. None of the tested compounds in any of the concentrations caused any tissue damage or irritation. The compounds were evaluated as non-irritant in the tested concentrations. This result is favorable for the intended use of the compounds in cosmetics.

Example 17: Evaluation of Eye Irritation in EpiOcular™

EpiOcular is a model of corneal epithelium manufactured by Mattek company. The effect of the tested substances is evaluated by MTT. A substance is considered irritant/corrosive if the absorbance of the formazane created by reduction of MTT is lower than 60 percent of value for negative control. Solutions (250 a 500 microM) of compounds 6-benzylamino-9-β-D-arabinofuranosylpurine, 6-furfurylamino-9-β-D-arabinofuranosylpurine and 6-(3-methoxybenzylamino)-9-β-D-arabinofuranosylpurin in the medium from the EpiOcular kit were tested in duplicates. The medium served as a negative control. The test was carried out according the manufacturer's manual the protocol for testing of liquid application forms. Only incubation time was increased from 30 min to 18 hours. The procedure is summarized below. After the delivery, the tissues were left in laboratory temperature for 15 min. After the integrity control and removal of agarose, the tissues were transferred into the wells of the 6-well plates containing 1 ml of cultivation medium. After 1 hour, the medium was exchanged for fresh one and the tissues were cultivated for 18 hours. Subsequently 20 microliters of DPBS without Ca2+ and Mg2+ (a component of the kit) was applied on the tissues, followed by 50 microliters of test solutions. After 18 hour incubation time, the tissues were removed from cultivation plate and washed out repeatedly in an excess of DPBS without Ca2+/Mg2+ (3 beakers with 100 ml). Subsequently the tissues were transferred to the wells of 12-well plates with 5 ml temperated medium and incubated for 12 minutes. After that, the tissues were transferred into the wells of 6-well plate with 1 ml of medium and incubated for 2 hours. Three hour incubation with MTT solution (1 mg/ml) was carried out in 24-well plates (0.3 ml of medium per well). After the incubation, the tissues were transferred to a new 24-well plate with 2 ml isopropanol per well. The plate was placed on a shaker and the resulting formazan was extracted for 3 hours. 200 microliters of the extracts were transferred to 96-well plate. Absorbance was measured at 570 nm and related to that of the negative control. All the tissue manipulation before the isopropanol extraction was carried out in sterile conditions. The cultivation was done in the standard cultivation conditions (CO2 5.5 percent, 37° C.), the cultivation medium and DPBS without $Ca^{2+}$ and $Mg^{2+}$ ions.

Conclusion: The relative viability of the tissues treated with the test compounds was 98-103%. The compounds in the tested concentration range do not cause irritation and can be favorably used in cosmetics including preparations that could be applied on face and the area around eyes.

Example 18: Anti-Senescent Activity of Novel Compounds Tested in Senescent Bioassay on Wheat Leaf Segments Seeds of winter wheat, *Triticum aestivum* cv. Hereward, were washed under running water for 24 hours and then sown on vermiculite soaked with Knop's solution. They were placed in the growth chamber at 25° C. with a 16/8 h light period at 50 $\mu mol \cdot m^{-2} \cdot s^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 µL, of the tested derivative solution each. The entire plate was inserted into a plastic box lined with paper tissues soaked in distilled water to prevent leaf sections from drying out. After 96 h incubation in the dark at 25° C., the leaves were removed and chlorophyll extracted by heating at 80° C. for 10 min in 5 mL of 80% ethanol (v/v). The sample volume was then restored to 5 mL by the addition of 80% ethanol (v/v). The absorbance of the extract was recorded at 665 nm. In addition, chlorophyll extracts from fresh leaves and leaf tips incubated in deionised water were measured. The results are means of five replicates and the entire test was repeated twice. In each experiment activities of the novel compounds were tested and compared with activity of BAP, which is known to be highly active cytokinin.

The compounds to be tested were dissolved in dimethylsulfoxide (DMSO) and the solution brought up to $10^{-3}$M with distilled water. This stock solution was further diluted with the respective media used for the biotest to a concentration ranging from $10^{-8}$M to $10^{-4}$M. The final concentration of DMSO did not exceed 0.2% and therefore did not affect the biological activity in the assay system used. The activity obtained for $10^{-4}$ M of BAP was postulated as 100%.

Newly developed compounds possess very strong antisenescent properties. Some of them cause 200% increase of chlorophyll content in detached wheat leaves in comparison to BAP.

TABLE 3

The effect of novel compounds on delaying senescence in detached leaf segments of *Triticum aestivum* cv. Hereward. The results are expressed in % of initial content of chlorophyll in fresh leaves before incubation.

| Compound | maximum effective concentration (mol · l$^{-1}$) | activity (%) [$10^{-4}$ mol · l$^{-1}$ BAP = 100%] |
|---|---|---|
| 6-furfurylamino-9-β-D-arabinofuranosylpurine | $10^{-4}$ | 193 ± 1 |
| 6-(3-methoxybenzylamino)-9-β-D-arabinofuranosylpurine | $10^{-4}$ | 118 ± 2 |
| 6-benzylaminopurine-9 β-D-deoxyribosylpurine | $10^{-4}$ | 178 ± 9 |
| 6-(3-chlorobenzylamino)-9-β-D-arabinofuranosylpurine | $10^{-4}$ | 172 ± 8 |
| 6-(3-fluorobenzylamino)-9-β-D-arabinofuranosylpurine | $10^{-4}$ | 195 ± 6 |
| 6-(2-bromobenzylamino)-9-β-D-arabinofuranosylpurine | $10^{-5}$ | 186 ± 19 |
| 6-(3-bromobenzylamino)-9-β-D-arabinofuranosylpurine | $10^{-4}$ | 198 ± 10 |
| 6-(4-bromobenzylamino)-9-β-D-arabinofuranosylpurine | $10^{-4}$ | 176 ± 11 |
| 6-(3-iodobenzylamino)-9-β-D-arabinofuranosylpurine | $10^{-4}$ | 198 ± 4 |
| 6-(3,4-dimethoxybenzylamino)-9-β-D-arabinofuranosylpurine | $10^{-4}$ | 147 ± 6 |
| 6-(3-chlorobenzylamino)-9-riboside (comparative example) | $10^{-4}$ | 72 ± 8 |
| 6-(3-iodobenzylamino)-9-riboside (comparative example) | $10^{-4}$ | 58 ± 19 |
| 6-(3-bromobenzylamino)-9-riboside (comparative example) | $10^{-4}$ | 89 ± 10 |
| 6-(3,4-dimethoxybenzylamino)-9-riboside (comparative example) | $10^{-4}$ | 47 ± 6 |
| 6-(2,4-dichlorbenzylamino)-9-riboside (comparative example) | $10^{-4}$ | 5 ± 1 |

Example 19: In Vitro Cytotoxic Activity of New Derivatives on Cancer Cell Lines One of the parameters used as the base for cytotoxic analysis is metabolic activity of viable cells, such as microtiter assay, which uses the Calcein AM, is now widely used to quantitate cell proliferation and cytotoxicity. The quantity of reduced Calcein AM corresponds to the number of viable cells in culture. The cell lines of breast cancer (MCF-7), mousse fibroblasts (NIH3T3), human erythromleukemia (K562) were used for routine screening of cytotoxicity of the compounds. The cells were maintened in Nunc/Corning 80 cm$^2$ plastic bottles and grown in media for cell culture (DMEM containing 5 g/l of glucose, 2 mM of glutamin, 100 U/ml of penicilin, 100 mg/ml of streptomycin, 10% of fetal bovine serum and sodium hydrogencarbonate). Cell suspensions were diluted according to cell types and according to expected final cell density ($10^4$ of cells per well according to characteristics of cell growth), pipetted 80 µl of cell suspension on 96-well microtiter plates. Innoculates were stabilized by 24 hrs preincubation at 37° C. in $CO_2$. Particular concentrations of tested compounds were added in time zero as 20 µl aliquotto wells of microtiter plates. Usually, the compounds were diluted into six concentrations in four-fold dilution series. In routine testing, the highest well concentration was 166.7 µM, of change dependent on the substance. All drug concentrations were examined in duplicates. The incubation of cells with tested derivatives lasted 72 hrs at 37° C., 100% humidity and in the atmosphere of $CO_2$. At the end of the incubation period, the cells were tested and analysed according to the addition of Calcein AM (Molecular probes) solution and the incubation lasted for next 1 hour. Fluorescence (FD) was measured using Labsystem FIA reader Fluorskan Ascent (Microsystems). The survival of tumor cells (The tumor cell survival-TCS) was counted according to equation: $GI_{50}=(FD_{well\ with\ derivative}/FD_{control\ well}) \times 100\%$. The value of $GI_{50}$, that is equal to the concentration of compound at which 50% of tumour cells are terminated. To evaluate the antitumor activity was tested toxicity of new derivatives on panel of cell lines of different histogenetic and species origin (Tab. 7, G150 concentration given in μM). It turned out that new compounds showed to be non toxic for neither of all tested tumor lines nor for nonmalignant cell line NIH3T3. Effective derivatives killed tumor cells in concentrations close to 0.1 to 50. None of the newly prepared compounds only reached the value.

TABLE 4

Cytotoxicity of newly prepared compounds for various tumour cell lines and NIH3T3

| Compound | MCF-7 | K562 | NIH3T3 |
| --- | --- | --- | --- |
| 6-benzylamino-9-ribosylpurine (comparative example) | 5.4 | 5.5 | 39 |
| 6-benzyl-9-β-D-arabinofuranosylpurine | >100 | >100 | >100 |
| 6-furfuryl-9-β-D-arabinofuranosylpurine | >100 | >100 | >100 |
| 6(3-methoxybenzylamino)-9-β-D-arabinofuranosylpurine | >100 | >100 | >100 |
| 6-benzylamino-9-β-D-deoxyribosylpurine | >100 | >100 | >100 |
| 3-methylbenzylamino-9-β-D-arabinofuranosylpurine | >100 | >100 | >100 |
| 4-methylbenzylamino-9-β-D-arabinofuranosylpurine | 95 | >100 | >100 |
| 2-methylbenzylamino-9-β-D-arabinofuranosylpurine | >100 | >100 | >100 |
| 3-fluorobenzylamino-9-β-D-arabinofuranosylpurine | >100 | >100 | >100 |
| 4-chlorobenzylamino-9-β-D-arabinofuranosylpurine | >100 | >100 | >100 |
| 2-fluorobenzylamino-9-β-D-arabinofuranosylpurine | 87 | >100 | >100 |
| 3-chlorobenzylamino-9-β-D-arabinofuranosylpurine | >100 | >100 | >100 |
| 4-hydroxybenzylamino-9-β-D-arabinofuranosylpurine | >100 | >100 | 87 |
| 3-fluorobenzylamino-9-β-D-2'-deoxyribosylpurine | >100 | >100 | >100 |
| 3-chlorobenzylamino-9-β-D-2'-deoxyribosylpurine | >100 | >100 | >100 |
| 3-hydroxybenzylamino-9-β-D-2'-deoxyribosylpurine | >100 | >100 | >100 |
| 2,4-dimethoxybenzylamino-9-β-D-arabinofuranosylpurine | 98 | >100 | >100 |
| 2-chloro-4-fluorobenzylamino-9-β-D-arabinofuranosylpurine | >100 | >100 | >100 |
| 3-chloro-4-fluorobenzylamino-9-β-D-arabinofuranosylpurine | >100 | >100 | >100 |

Example 20: In Vitro Test of Phototoxic Effects of 6-(3-methoxybenzylamino)-9-β-D-arabinofuranosylpurine on Normal Human Dermal Fibroblasts Phototoxic potential of test compound was determined by modified in vitro test validated phototoxicity evaluation (Spielmann H, Balls M, Dupuis J, Pape W J, Pechovitch G, de Silva O, Holzhater H G, Clothier R, Desolle P, Gerberick F, Liebsch M, Lovell W W, Maurer T, Pfannenbecker U, Potthast J M, Csato M, Sladowski D, Steiling W, Brantom P., Toxicol In Vitro. 1998 Jun. 1; 12(3):305-27). Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacký University, Olomouc and all patients signed written informed consent. Fibroblasts were used between the 2nd and 4th passage. For all experiments the fibroblasts were seeded onto 96-well plates at a density of $0.8 \times 10^5$ cells/ml (0.2 ml per well) of cultivation medium (DMEM supplemented with foetal calf serum (10%, v/v), penicillin (100 mg/ml) and streptomycin (100 U/ml)).

Test compound was 6-(3-methoxybenzylamino)-9-β-D-arabinofuranosylpurine. Compound was dissolved in DMSO and then diluted in serum free medium (DMEM supplemented with penicillin (100 mg/ml) and streptomycin (100 U/ml)). The final applied concentrations of the compound 0.39-125 μmol/l. As a control, serum free medium supplemented with appropriate concentration of DMSO (0.5%, v/v) was used. In parallel with test compounds, chlorpromazine (CPZ; 0.39-100 μmol/l) was used as a known phototoxic compound. The test compound was in parallel applied on two 96-well plates with NHDF. After 60 minutes incubation with test compound medium was discarded, cells were washed two-times with PBS and PBS supplemented with glucose (1 mg/ml) was applied. A plate was then exposed to a non-cytotoxic dose of UVA radiation (5.0 J/cm$^2$) using a solar simulator SOL 500 (Dr. Hoenle Technology, Germany) equipped with a H1 filter transmitting wavelengths of 320-400 nm. Intensity of UVA radiation was evaluated before each irradiation by UVA-meter. A control (non-irradiated) plate was for the period of irradiation incubated in dark. After UVA exposure PBS with glucose was discarded and serum free medium was applied. After 24 hours (37° C., 5% CO$_2$) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl$_2$ (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetition with use of cells from four donors to minimize individual sensitivity of donor cells. Phototoxic effect was evaluated as % of viability of control cells that was calculated from experimental data (absorbance) according to the following equation:

$$\text{Viability (\% of control)} = \left(\frac{(A_S - A_B)}{(A_C - A_B)}\right) \cdot 100$$

$A_S$ . . . absorbance of sample (cells pre-incubated with test compound in serum free medium and irradiated)
$A_C$ . . . absorbance of control (cells pre-incubated with DMSO in serum free medium and irradiated)
$A_B$ . . . absorbance of background (extraction solution)

Figure 3:
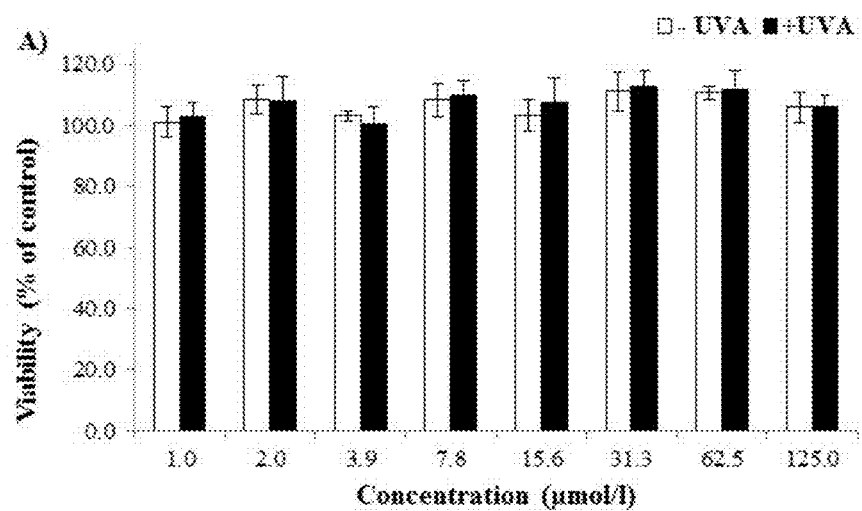
FIG. 3. UVA-induced effects of test compounds on NHDF viability of 6(3-methoxybenzylamino)-9-β-D-arabinofuranosylpurine (Example 20).
Figure 4:
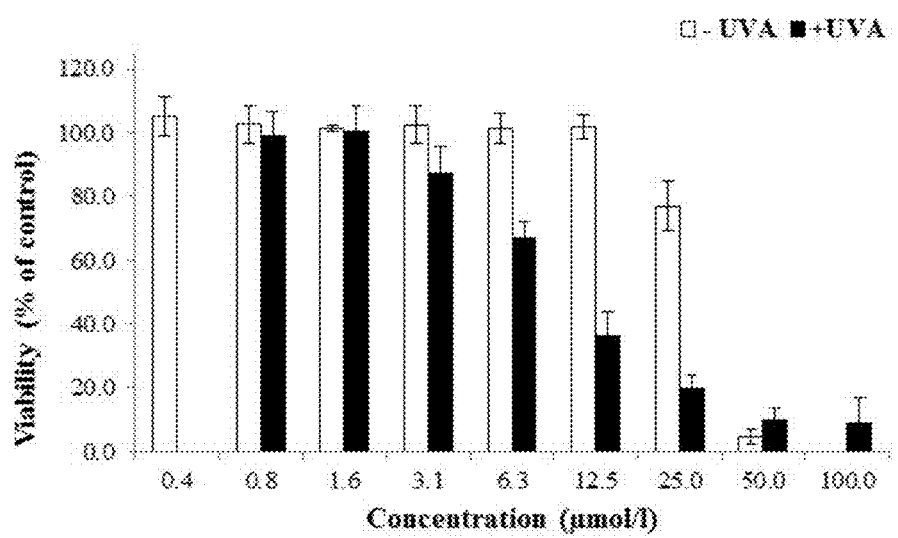
FIG. 4. UVA-induced effect of chlorpromazine on NHDF viability (Example 20).

Result: Treatment with test compounds and following exposure to non-toxic UVA dose did not cause decrease in cell viability~incorporation of NR and thus test compound can be considered as non-phototoxic in the used concentration range (0.9-125 μmol/l or 3.9-500 μmol/l). Results are given in FIG. 3. Effect of a well-known phototoxic compound chlorpromazine (Spielmann H, Balls M, Dupuis J, Pape W J, Pechovitch G, de Silva O, Holzhater H G, Clothier R, Desolle P, Gerberick F, Liebsch M, Lovell W W, Maurer T, Pfannenbecker U, Potthast J M, Csato M, Sladowski D, Steiling W, Brantom P., Toxicol In Vitro. 1998 Jun. 1; 12(3):305-27), used as positive control is demonstrated in FIG. 4. Above data indicate that test compounds are safe for cosmetic and dermatological application including use with following exposure of treated skin with solar radiation.

Example 21: In Vitro Test of Photoprotective Effects of 6(3-methoxybenzylamino)-9-β-D-arabinofuranosylpurine on Dermal Fibroblasts Normal human dermal fibroblasts (NHDF) were used as an in vitro model. Cells were isolated from tissue specimens obtained from healthy patients undergoing plastic surgery at the Department of Plastic and Aesthetic Surgery (University Hospital Olomouc). The use of skin tissue was in accordance with the Ethics Committee of the University Hospital and Faculty of Medicine and Dentistry, Palacký University, Olomouc and all patients signed written informed consent. Fibroblasts were used between the 2nd and 4th passage. For all experiments the fibroblasts were seeded onto 96-well plates at a density of $0.8 \times 10^5$ cells/ml (0.2 ml per well) of cultivation medium (DMEM supplemented with foetal calf serum (10%, v/v), penicillin (100 mg/ml) and streptomycin (100 U/ml)).

Test compounds included 6-(3-methoxybenzylamino)-9-β-D-arabinofuranosylpurine. Compounds were dissolved in DMSO and then diluted in serum free medium (DMEM supplemented with penicillin (100 mg/ml) and streptomycin (100 U/ml)). The final applied concentrations of 6(3-methoxybenzylamino)-9-β-D-arabinofuranosylpurine were 0.9; 1.8; 3.9 a 7.8 μmol/l. As a control serum free medium supplemented with appropriate concentration of DMSO (0.5%, v/v) was used. Each test compound was in parallel applied on two 96-well plates with NHDF. After 60 minutes incubation medium with test compound was discarded, cells were washed two-times with PBS and PBS supplemented with glucose (1 mg/ml) was applied. To study UVA photoprotection, a plate was exposed to a cytotoxic dose of UVA radiation (7.5 J/cm$^2$) using a solar simulator SOL 500 (Dr. Hoenle Technology, Germany) equipped with a H1 filter transmitting wavelengths of 320-400 nm. To study UVB photoprotection, a plate was exposed to a cytotoxic dose of UVB radiation (400 mJ/cm$^2$) using the solar simulator equipped with a H2 filter transmitting wavelengths of 295-320 nm. Intensity of UVA or UVB radiation was evaluated before each irradiation by UVA- or UVB-meter. Control (non-irradiated) plates were for the period of irradiation incubated in dark. After UVA or UVB exposure PBS with glucose was discarded and serum free medium was applied. After 24 hours (37° C., 5% CO$_2$) cell damage was evaluated by neutral red (NR) incorporation into viable cells. Medium was discarded and NR solution (0.03% w/v, PBS) was applied. After 60 minutes NR solution was discarded, cells were fixed with a mixture of formaldehyde (0.5%, v/v) and CaCl$_2$ (1%, m/v) in ratio 1:1 and then NR was dissolved in methanol (50%, v/v) with acetic acid (1%, v/v). After 5 minutes of intensive shaking absorbance was measured at 540 nm. Experiments were performed in four independent repetition with use of cells from four donors to minimize individual sensitivity of donor cells. Photoprotective effect was evaluated by comparison of experimental data (absorbance) of test compounds with a positive control and a negative control (according to the following equation:

$$\text{Protection (\%)} = 100 - \left| \frac{As - Anc}{Apc - Anc} \right| \cdot 100$$

As . . . absorbance of sample (cells pre-incubated with test compounds in serum free medium and irradiated)
Anc . . . absorbance of negative control (cells pre-incubated with s DMSO in serum free medium and non-irradiated=incubated in dark)
Apc . . . absorbance of positive control (cells pre-incubated with s DMSO in serum free medium and irradiated)

Figure 5:
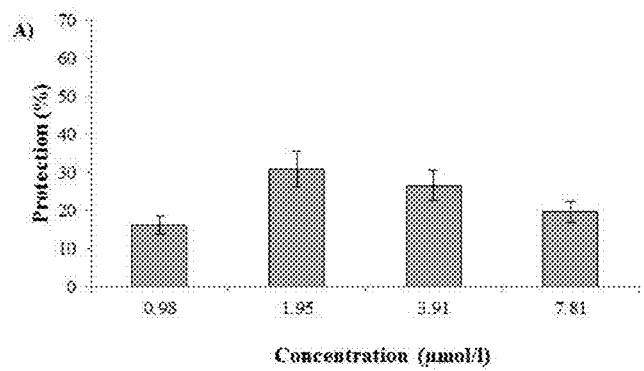
FIG. 5. Effect of test compounds on UVA-induced damage to NHDF. (A) 6(3-methoxybenzylamino)-9-β-D-arabinofuranosylpurine (Example 21).
Figure 6:
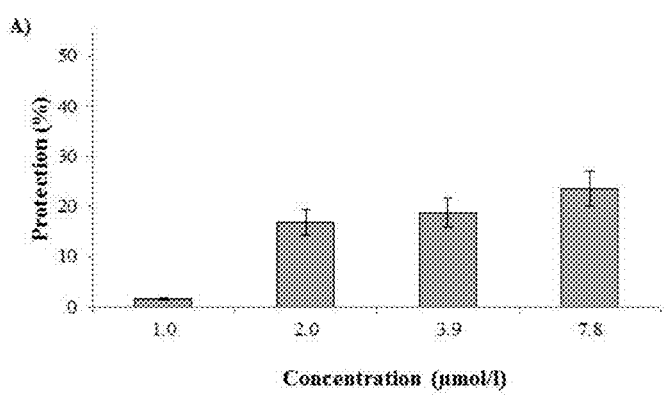
FIG. 6. Effect of test compounds on UVB-induced damage to NHDF. (A) 6(3-methoxybenzylamino)-9-β-D-arabinofuranosylpurine (Example 21).

Results: Cells pre-incubated with test compounds and exposed to UVA or UVB radiation showed higher viability (ability to incorporate NR) compared to those pre-incubated with DMSO (control) and UVA or UVB irradiated (FIGS. 5 and 6). Therefore test compound has high photoprotective potential.

Example 19: Differential Gene Expression Study

Comparative gene expression analysis in *Arabidopsis* model was performed to gain information about the reprogramming of gene transcription when senescent leaves were treated with 6-(3-methoxybenzylamino)-9-β-D-arabinofuranosylpurine (3MeOBAPA).

Figure 7:
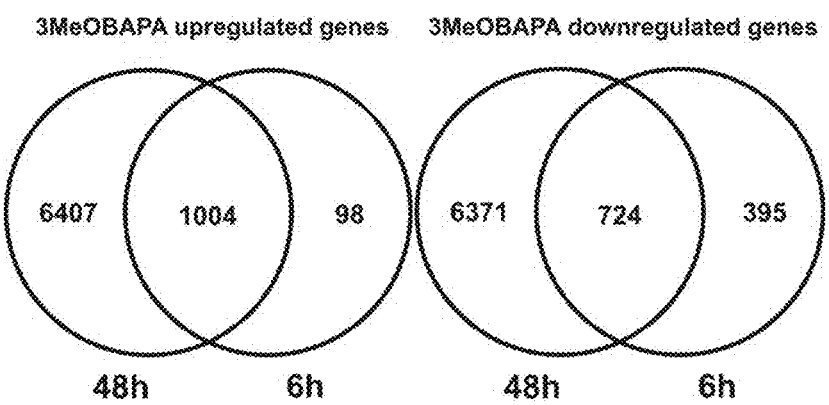
FIG. 7. Venn diagrams of 3MeOBAPA-responsive genes as revealed in the short-term (6 h) and long-term (48 h) treatments (Example 22).

For isolation of total RNA, *Arabidopsis* wild-type plants (Col-0) were used, which were either treated with 3MeOBAPA or left untreated. Wild-type plants were grown in soil for 30 days, and then leaves of similar size and chlorophyll content were cut and immediately used for the treatment. At least 20 detached leaves were submerged in 1×MS medium supplemented with 10 μM 3MeOBAPA. Control samples were mock treated with DMSO only. After incubation for 6 h or 48 h in the dark, detached leaves were frozen in liquid nitrogen and used for RNA isolation; 150 mg of liquid nitrogen-ground material was used per isolation. cDNA sequencing libraries were prepared with the Illumina TruSeq Stranded mRNA LT Sample Prep Kit (Illumina, San Diego, Calif.) according to standard Illumina's protocols and sequenced on HiSeq 2500 apparatus (50 bp single-end reads). Data were subjected to differential transcriptomic analysis with the aim to reveal significantly regulated genes and their expression levels. To gain insight into the molecular mechanism of 3MeOBAPA action in *Arabidopsis* we decided to analyze the gene expression patterns via comparison of mock (DMSO)-treated plants with those obtained after i) short time treatment with 3MeOBAPA (6 h) and ii) long time treatment (48 h). This comparison leads to identification of group of genes with similar kinetic of expression and helps to understand possible mechanism of regulation. For data analysis, we performed ab initio method where sequencing reads were mapped to the reference genome. The short time treatment resulted in reprogramming of the gene transcription compared to the mock-treated control with 1119 downregulated and 1102 upregulated genes (P≤0.05). Further treatment with 3MeOBAPA (i.e. 48 h) led to alterations in the expression profiles and, thus, we could observe more profound changes in the numbers of affected genes: 7095 genes were downregulated and 7509 genes were upregulated (P≤0.05). Analysis of regulated genes in both groups (short time treatment vs. long time treatment) showed a substantial overlap in the two categories. Indeed, we could detect 1102 genes that were upregulated in response to 3MeOBAPA treatment and 724 genes that were downregulated in both groups (FIG. 7). The overlap is particularly visible in the group of upregulated genes suggesting a rapid response to the elicitation after 6 h treatment that reaches maximal values after 48 h incubation with 3MeOBAPA. This trend is well documented in the list of top 50 genes upregulated in response to 3MeOBAP treatment (Tab. 1). As evident, all genes that were upregulated after 6 h of the treatment probably remain activated over a period of 48 h and their expression levels in the latter time point are one or two orders of magnitude higher than those recorded in 6 h.

A closer inspection of the top 50 3MeOBAPA upregulated genes reveals that several most abundant gene transcripts present in both groups are related directly to plant defense mechanisms (Tab. 5). This was the case of plant defensins family proteins including At5g44430 coding for defensin-like protein 1.2C, At5g44420 coding for defensin-like protein 1.2A, At2g26020 coding for defensin-like protein 1.2B or At2g26010 coding for defensin-like protein 1.3 which are important anti-stress factors upregulated in response to pathogen or stress elicitation and, importantly, also during plant senescence. Moreover, we also detected high expression levels of several enzymes involved in modifications and in remodeling of cell wall that are also important for pollen tube growth. These enzymes belong either to pectin methylesterase or pectin lyase families, such as At2g47040 coding for pectin methylesterase Vanguard1 and At3g07820 coding for pectin lyase-like superfamily protein, or, interestingly, there were also genes coding for enzymes with combined pectin methylesterase/pectin methylesterase inhibitor activity such as At2g47050 or At3g05610. Other enzymes of cell wall synthesis were also detected such as products of gene At4g35010 coding for β-galactosidase 11 (BGAL11), At1g02790 coding for polygalacturonase 4 (PGA4) or At3g62710 coding for glycosyl hydrolase family protein. This strongly suggests that in plants 3MeOBAP specifically regulates processes that are necessary for cell wall remodeling and consequent enhanced resistance to stresses and fungal pathogens.

TABLE 5

Top 50 genes upregulated in response to 3MeOBAPA treatment in two selected time points. Genes with P ≤ 0.05 that are changed both after 6 h and after 48 h of treatment with 10 μM 3MeOBAP are shown.

| AGI code | Description | logFC 6 h | logFC 48 h |
|---|---|---|---|
| AT2G47040 | Pectin methylesterase Vanguard1 (VGD1) | 2.80 | 5.89 |
| AT2G47050 | Plant invertase/pectin methylesterase inhibitor superfamily protein | 2.31 | 5.82 |
| AT3G07820 | Pectin lyase-like superfamily protein | 2.22 | 6.45 |
| AT4G35010 | Beta-galactosidase 11 (BGAL11) | 2.03 | 5.33 |
| AT3G05610 | Pectinesterase/pectinesterase inhibitor 21 (PME21) | 1.80 | 5.58 |
| AT5G44430 | Defensin-like protein 1.2C (PDF1.2C) | 1.75 | 8.87 |
| AT1G55560 | SKU5 similar 14 (SKS14) | 1.71 | 8.75 |
| AT1G02790 | Polygalacturonase 4 (PGA4) | 1.67 | 8.59 |
| AT5G44420 | Defensin-like protein 1.2A (PDF1.2A) | 1.58 | 8.15 |
| AT2G26020 | Defensin-like protein 1.2B (PDF1.2B) | 1.52 | 6.04 |
| AT2G26010 | Defensin-like protein 1.3 (PDF1.3) | 1.47 | 8.23 |
| AT5G45880 | Pollen Ole e 1 allergen and extensin family protein | 1.45 | 5.52 |
| AT3G62710 | Glycosyl hydrolase family protein | 1.35 | 5.26 |
| AT5G12960 | Putative glycosyl hydrolase | 1.33 | 5.26 |
| AT1G05580 | Cation/H(+) exchanger 23 (CHX23) | 1.26 | 5.46 |
| AT2G04460 | Transposable element gene | 1.16 | 5.43 |
| AT5G61160 | Agmatine coumaroyltransferase (ACT) | 1.13 | 5.05 |
| AT1G59950 | NAD(P)-linked oxidoreductase superfamily protein | 1.08 | 5.72 |
| AT1G75830 | Defensin-like protein 1.1 (PDF1.1) | 1.06 | 7.85 |
| AT3G28153 | Transposable element gene | 0.92 | 5.70 |
| AT2G28210 | Alpha carbonic anhydrase 2 (ATACA2) | 0.85 | 5.86 |
| AT3G13400 | SKU5 similar 13 (SKS13) | 0.82 | 5.57 |
| AT4G01390 | TRAF-like family protein | 0.79 | 6.24 |
| AT1G76640 | Calcium-binding EF-hand family protein (CML39) | 0.78 | 7.06 |
| AT2G18150 | Peroxidase 15 (PER15) | 0.68 | 7.22 |
| AT4G24350 | Phosphorylase superfamily protein | 0.64 | 6.45 |
| AT1G19670 | Chlorophyllase-1 (CLH1) | 0.63 | 6.42 |
| AT3G28155 | ARM repeat superfamily protein | 0.59 | 6.06 |
| AT1G15540 | 2-oxoglutarate and Fe(II)-dependent oxygenase superfamily protein | 0.57 | 5.63 |
| AT5G52670 | Copper transport family protein | 0.57 | 6.03 |
| AT5G63270 | RPM1-interacting protein 4 (RIN4) family protein | 0.56 | 7.11 |
| AT2G39030 | L-ornithine N5-acetyltransferase (NATA1) | 0.56 | 5.48 |
| AT4G21830 | Peptide methionine sulfoxide reductase B7 (MSRB7) | 0.55 | 5.95 |
| AT3G09340 | Transmembrane amino acid transporter family protein | 0.55 | 8.54 |
| AT2G02010 | Glutamate decarboxylase 4 (GAD4) | 0.55 | 5.09 |
| AT2G21900 | WRKY transcription factor 59 (WRKY59) | 0.54 | 5.81 |
| AT4G26010 | Peroxidase 44 (PER44) | 0.53 | 7.92 |
| AT3G11340 | UDP-Glycosyltransferase superfamily protein | 0.51 | 6.60 |
| AT2G26695 | Ran BP2/NZF zinc finger-like superfamily protein | 0.50 | 5.90 |
| AT1G59860 | 17.6 kDa class I heat shock protein 1 (HSP17.6A) | 0.48 | 5.47 |
| AT4G22620 | SAUR-like auxin-responsive family protein | 0.46 | 5.05 |
| AT4G39320 | Microtubule-associated protein-related | 0.45 | 5.09 |
| AT5G62720 | Integral membrane HPP family protein | 0.44 | 5.31 |
| AT2G37430 | Zinc finger protein ZAT11 | 0.42 | 4.96 |
| AT5G03610 | GDSL esterase/lipase | 0.42 | 4.61 |
| AT4G37780 | Myb domain protein 87 (MYB87) | 0.41 | 6.88 |
| AT4G22030 | F-box domain, cyclin-like, F-box domain, Skp2-like protein | 0.41 | 5.02 |
| AT1G10585 | Basic helix-loop-helix (bHLH) DNA-binding superfamily protein | 0.38 | 4.85 |

TABLE 5-continued

Top 50 genes upregulated in response to 3MeOBAPA treatment in two
selected time points. Genes with P ≤ 0.05 that are changed both
after 6 h and after 48 h of treatment with 10 μM 3MeOBAP are shown.

| AGI code | Description | logFC 6 h | logFC 48 h |
|---|---|---|---|
| AT3G44830 | Putative phospholipid: diacylglycerol acyltransferase 2 (PDAT2) | 0.38 | 4.91 |
| AT4G31950 | Cytochrome P450 82C3 (CYP82C3) | 0.37 | 5.29 |

The invention claimed is:

1. A Method for regulation of aging in animals and/or for photoprotection of animals for cosmetic or therapeutic purposes, comprising the step of administering to an animal, who is in need of cosmetic or therapeutic treatment, a therapeutically effective or cosmetically effective amount of a 6-aryl-9-glycosidpurine of formula I

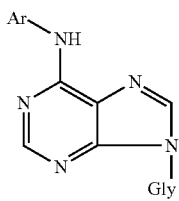

or a pharmaceutically acceptable salt thereof with alkali metal, ammonia, amine, or addition salt with acid, wherein Gly represents β-D-arabinofuranosyl or β-D-2'-deoxyribofuranosyl, Ar represents benzyl or furfuryl, each of which can be unsubstituted or substituted by one or more, preferably one to three, substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy.

2. A method for regulating aging and/or UV photodamage in cells or microorganisms wherein an effective amount of at least one compound of formula I

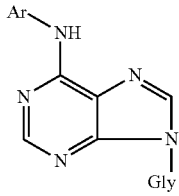

or a pharmaceutically acceptable salt thereof with alkali metal, ammonia, amine, or addition salt with acid, wherein Gly represents β-D-arabinofuranosyl or β-D-2'-deoxyribofuranosyl, Ar represents benzyl or furfuryl, each of which can be unsubstituted or substituted by one or more substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy, is applied to cells or microorganisms in need of regulation of aging and/or UV photodamage.

3. The method according to claim 1, wherein the compound of formula I is selected from the group consisting of:
6-furfurylamino-9-β-D-arabinofuranosylpurine,
6-(3-methylfurfurylamino)-9-β-D-arabinofuranosylpurine,
6-(4-methylfurfurylamino)-9-β-D-arabinofuranosylpurine,
6-(5-methylfurfurylamino)-9-β-D-arabinofuranosylpurine,
6-(3-fluorofurfurylamino)-9-β-D-arabinofuranosylpurine,
6-(4-fluorofurfurylamino)-9-β-D-arabinofuranosylpurine,
6-(5-fluorofurfurylamino)-9-β-D-arabinofuranosylpurine,
6-(3-chlorofurfurylamino)-9-β-D-arabinofuranosylpurine,
6-(4-chlorofurfurylamino)-9-β-D-arabinofuranosylpurine,
6-(5-chlorofurfurylamino)-9-β-D-arabinofuranosylpurine,
6-(3-bromofurfurylamino)-9-β-D-arabinofuranosylpurine,
6-(4-bromofurfurylamino)-9-β-D-arabinofuranosylpurine,
6-(5-bromofurfurylamino)-9-β-D-arabinofuranosylpurine,
6-(3-hydroxyfurfurylamino)-9-β-D-arabinofuranosylpurine,
6-(4-hydroxyfurfurylamino)-9-β-D-arabinofuranosylpurine,
6-(5-hydroxyfurfurylamino)-9-β-D-arabinofuranosylpurine,
6-(3-methoxyfurfurylamino)-9-β-D-arabinofuranosylpurine,
6-(4-methoxyfurfurylamino)-9-β-D-arabinofuranosylpurine,
6-(5-methoxyfurfurylamino)-9-β-D-arabinofuranosylpurine,
6-(2-aminofurfurylamino)-9-β-D-arabinofuranosylpurine,
6-(3-aminofurfurylamino)-9-β-D-arabinofuranosylpurine,
6-(4-aminofurfurylamino)-9-β-D-arabinofuranosylpurine,
6-(3,4-dihydroxyfurfurylamino)-9-β-D-arabinofuranosylpurine,
6-(3,5-dihydroxyfurfurylamino)-9-β-D-arabinofuranosylpurine, 6-(3,4-dihydroxyfurfurylamino)-9-β-D-arabinofuranosylpurine,
6-(2,4-dihydroxyfurfurylamino)-9-β-D-arabinofuranosylpurine,
6-(2,5-dihydroxyfurfurylamino)-9-β-D-arabinofuranosylpurine,
6-(2,6-dihydroxyfurfurylamino)-9-β-D-arabinofuranosylpurine,
6-(3,4-dimethoxyfurfurylamino)-9-β-D-arabinofuranosylpurine,
6-(3,4-dimethoxyfurfurylamino)-9-β-D-arabinofuranosylpurine,
6-(3,5-dimethoxyfurfurylamino)-9-β-D-arabinofuranosylpurine,
6-(2,3-dimethoxyfurfurylamino)-9-β-D-arabinofuranosylpurine,
6-(2,4-dimethoxyfurfurylamino)-9-β-D-arabinofuranosylpurine,
6-(2,5-dimethoxyfurfurylamino)-9-β-D-arabinofuranosylpurine,
6-(2,6-dimethoxyfurfurylamino)-9-β-D-arabinofuranosylpurine,
6-(2-hydroxy-3-methoxyfurfurylamino)-9-β-D-arabinofuranosylpurine,
6-(2-hydroxy-4-methoxyfurfurylamino)-9-β-D-arabinofuranosylpurine,
6-(2-hydroxy-5-methoxyfurfurylamino)-9-β-D-arabinofuranosylpurine,
6-(2-hydroxy-6-methoxyfurfurylamino)-9-β-D-arabinofuranosylpurine,
6-(3-hydroxy-2-methoxyfurfurylamino)-9-β-D-arabinofuranosylpurine,
6-(3-hydroxy-4-methoxyfurfurylamino)-9-β-D-arabinofuranosylpurine,
6-(3-hydroxy-5-methoxyfurfurylamino)-9-β-D-arabinofuranosylpurine,
6-(3-hydroxy-6-methoxyfurfurylamino)-9-β-D-arabinofuranosylpurine,
6-(4-hydroxy-2-methoxyfurfurylamino)-9-β-D-arabinofuranosylpurine,
6-(4-hydroxy-3-methoxyfurfurylamino)-9-β-D-arabinofuranosylpurine,
6-(4-hydroxy-5-methoxyfurfurylamino)-9-β-D-arabinofuranosylpurine,
6-(4-hydroxy-6-methoxyfurfurylamino)-9-β-D-arabinofuranosylpurine,
6-(2-fluorobenzylamino)-9-β-D-arabinofuranosylpurine,
6-(3-fluorobenzylamino)-9-β-D-arabinofuranosylpurine,
6-(4-fluorobenzylamino)-9-β-D-arabinofuranosylpurine,
6-(2-bromobenzylamino)-9-β-D-arabinofuranosylpurine,
6-(3-bromobenzylamino)-9-β-D-arabinofuranosylpurine,
6-(4-bromobenzylamino)-9-β-D-arabinofuranosylpurine,
6-(2-iodobenzylamino)-9-β-D-arabinofuranosylpurine,
6-(3-iodobenzylamino)-9-β-D-arabinofuranosylpurine,
6-(4-iodobenzylamino)-9-β-D-arabinofuranosylpurine,
6-(2-chlorobenzylamino)-9-β-D-arabinofuranosylpurine,
6-(2-chlorobenzylamino)-9-β-D-arabinofuranosylpurine,
6-(3-chlorobenzylamino)-9-β-D-arabinofuranosylpurine,
6-(4-chlorobenzylamino)-9-β-D-arabinofuranosylpurine,
6-(2-methoxybenzylamino)-9-β-D-arabinofuranosylpurine,
6-(3-methoxybenzylamino)-9-β-D-arabinofuranosylpurine,
6-(4-methoxybenzylamino)-9-β-D-arabinofuranosylpurine,
6-(2-hydroxybenzylamino)-9-β-D-arabinofuranosylpurine,
6-(3-hydroxybenzylamino)-9-β-D-arabinofuranosylpurine,
6-(4-hydroxybenzylamino)-9-β-D-arabinofuranosylpurine,
6-(4-hexylbenzylamino)-9-β-D-arabinofuranosylpurine,
6-(2-fluoro-6-(trifluoromethyl)benzylamino)-9-β-D-arabinofuranosylpurine,
6-(3-chloro-2,6-difluorobenzylamino)-9-β-D-arabinofuranosylpurine,
6-(3-(trifluoromethylthio)benzylamino)-9-β-D-arabinofuranosylpurine,
6-(2-chloro-3,6-difluorobenzylamino)-9-β-D-arabinofuranosylpurine,
6-(4-(trifluoromethylthio)benzylamino)-9-β-D-arabinofuranosylpurine,
6-(3-fluoro-5-(trifluoromethyl)benzylamino)-9-β-D-arabinofuranosylpurine,
6-(2-chloro-4-fluorobenzylamino)-9-β-D-arabinofuranosylpurine,
6-(2-(trifluoromethoxy)benzylamino)-9-β-D-arabinofuranosylpurine,
6-(3-(trifluoromethyl)benzylamino)-9-β-D-arabinofuranosylpurine,
6-(2-(trifluoromethyl)benzylamino)-9-β-D-arabinofuranosylpurine,
6-(4-(trifluoromethyl)benzylamino)-9-β-D-arabinofuranosylpurine,
6-(4-chloro-3-(trifluoromethyl)benzylamino)-9-β-D-arabinofuranosylpurine,
6-(4-fluoro-3-(trifluoromethyl)benzylamino)-9-β-D-arabinofuranosylpurine,
6-(3,5-bis(trifluoromethyl)benzylamino)-9-β-D-arabinofuranosylpurine,
6-(3-(trifluoromethoxy)benzylamino)-9-β-D-arabinofuranosylpurine,
6-(4-(trifluoromethoxy)benzylamino)-9-β-D-arabinofuranosylpurine,
6-(4-(trifluoromethyl)benzylamino)-9-β-D-arabinofuranosylpurine,
6-(2-aminobenzylamino)-9-β-D-arabinofuranosylpurine,
6-(3-aminobenzylamino)-9-β-D-arabinofuranosylpurine,
6-(4-aminobenzylamino)-9-β-D-arabinofuranosylpurine,
6-(4-diethylaminobenzylamino)-9-β-D-arabinofuranosylpurine,
6-(3,4-dihydroxybenzylamino)-9-β-D-arabinofuranosylpurine,
6-(3,5-dihydroxybenzylamino)-9-β-D-arabinofuranosylpurine,
6-(3,4-dihydroxybenzylamino)-9-β-D-arabinofuranosylpurine,
6-(2,4-dihydroxybenzylamino)-9-β-D-arabinofuranosylpurine,
6-(2,5-dihydroxybenzylamino)-9-β-D-arabinofuranosylpurine,
6-(2,6-dihydroxybenzylamino)-9-β-D-arabinofuranosylpurine,
6-(3,4-dimethoxybenzylamino)-9-β-D-arabinofuranosylpurine,
6-(3,4-dimethoxybenzylamino)-9-β-D-arabinofuranosylpurine,
6-(3,5-dimethoxybenzylamino)-9-β-D-arabinofuranosylpurine,
6-(2,3-dimethoxybenzylamino)-9-β-D-arabinofuranosylpurine,
6-(2,4-dimethoxybenzylamino)-9-β-D-arabinofuranosylpurine, 6-(2,5-dimethoxybenzylamino)-9-β-D-arabinofuranosylpurine,
6-(2,6-dimethoxybenzylamino)-9-β-D-arabinofuranosylpurine,
6-(2-hydroxy-3-methoxybenzylamino)-9-β-D-arabinofuranosylpurine,
6-(2-hydroxy-4-methoxybenzylamino)-9-β-D-arabinofuranosylpurine,
6-(2-hydroxy-5-methoxybenzylamino)-9-β-D-arabinofuranosylpurine,
6-(2-hydroxy-6-methoxybenzylamino)-9-β-D-arabinofuranosylpurine,
6-(3-hydroxy-2-methoxybenzylamino)-9-β-D-arabinofuranosylpurine,
6-(3-hydroxy-4-methoxybenzylamino)-9-β-D-arabinofuranosylpurine,
6-(3-hydroxy-5-methoxybenzylamino)-9-β-D-arabinofuranosylpurine,
6-(3-hydroxy-6-methoxybenzylamino)-9-β-D-arabinofuranosylpurine,
6-(4-hydroxy-2-methoxybenzylamino)-9-β-D-arabinofuranosylpurine,
6-(4-hydroxy-3-methoxybenzylamino)-9-β-D-arabinofuranosylpurine,
6-(4-hydroxy-5-methoxybenzylamino)-9-β-D-arabinofuranosylpurine,
6-(4-hydroxy-6-methoxybenzylamino)-9-β-D-arabinofuranosylpurine,
6-(2,3,4-trimethoxybenzylamino)-9-β-D-arabinofuranosylpurine,
6-(2,4,5-trimethoxybenzylamino)-9-β-D-arabinofuranosylpurine,
6-(2,4,6-trimethoxybenzylamino)-9-β-D-arabinofuranosylpurine,
6-(3,4,5-trimethoxybenzylamino)-9-β-D-arabinofuranosylpurine,
6-(2-hydroxy-3,4,5-trimethoxybenzylamino)-9-β-D-arabinofuranosylpurine,
6-(2-hydroxy-3,4,6-trimethoxybenzylamino)-9-β-D-arabinofuranosylpurine,
6-(2-hydroxy-4,5,6-trimethoxybenzylamino)-9-β-D-arabinofuranosylpurine,
6-(2,4,6-trimethoxybenzylamino)-9-β-D-arabinofuranosylpurine,
6-(2,3,4-trihydroxybenzylamino)-9-β-D-arabinofuranosylpurine,
6-(2,4,6-trihydroxybenzylamino)-9-β-D-arabinofuranosylpurine,
6-(2,3,4-trihydroxybenzylamino)-9-β-D-arabinofuranosylpurine,
6-(3,4,5-trihydroxybenzylamino)-9-β-D-arabinofuranosylpurine,
6-(2,4,6-trihydroxybenzylamino)-9-β-D-arabinofuranosylpurine,
6-(2-hydroxy-3-chlorobenzylamino)-9-β-D-arabinofuranosylpurine,
6-(2-hydroxy-4-chlorobenzylamino)-9-β-D-arabinofuranosylpurine,
6-(2-hydroxy-5-chlorobenzylamino)-9-β-D-arabinofuranosylpurine,
6-(2-hydroxy-6-chlorobenzylamino)-9-β-D-arabinofuranosylpurine,
6-(2-hydroxy-3-iodobenzylamino)-9-β-D-arabinofuranosylpurine,
6-(2-hydroxy-4-iodobenzylamino)-9-β-D-arabinofuranosylpurine,
6-(2-hydroxy-5-iodobenzylamino)-9-β-D-arabinofuranosylpurine,
6-(2-hydroxy-6-iodobenzylamino)-9-β-D-arabinofuranosylpurine,
6-(2-hydroxy-3-bromobenzylamino)-9-β-D-arabinofuranosylpurine,
6-(2-hydroxy-4-bromobenzylamino)-9-β-D-arabinofuranosylpurine,
6-(2-hydroxy-5-bromobenzylamino)-9-β-D-arabinofuranosylpurine,
6-(2-hydroxy-6-bromobenzylamino)-9-β-D-arabinofuranosylpurine,
6-(2-hydroxy-3-fluorobenzylamino)-9-β-D-arabinofuranosylpurine,
6-(2-hydroxy-4-fluorobenzylamino)-9-β-D-arabinofuranosylpurine,
6-(2-hydroxy-5-fluorobenzylamino)-9-β-D-arabinofuranosylpurine,
6-(3-methylfurfurylamino)-9-β-D-2'-deoxyribofuranosylpurine,
6-(4-methylfurfurylamino)-9-β-D-2'-deoxyribofuranosylpurine, 6-(5-methylfurfurylamino)-9-β-D-2'-deoxyribofuranosylpurine,
6-(3-fluorofurfurylamino)-9-β-D-2'-deoxyribofuranosylpurine,
6-(4-fluorofurfurylamino)-9-β-D-2'-deoxyribofuranosylpurine,
6-(5-fluorofurfurylamino)-9-β-D-2'-deoxyribofuranosylpurine,
6-(3-chlorofurfurylamino)-9-β-D-2'-deoxyribofuranosylpurine,
6-(4-chlorofurfurylamino)-9-β-D-2'-deoxyribofuranosylpurine,
6-(5-chlorofurfurylamino)-9-β-D-2'-deoxyribofuranosylpurine,
6-(3-bromo-furfurylamino)-9-β-D-2'-deoxyribofuranosylpurine,
6-(4-bromofurfurylamino)-9-β-D-2'-deoxyribofuranosylpurine,
6-(5-bromofurfurylamino)-9-β-D-2'-deoxyribofuranosylpurine,
6-(3-hydroxyfurfurylamino)-9-β-D-2'-deoxyribofuranosylpurine,
6-(4-hydroxyfurfurylamino)-9-β-D-2'-deoxyribofuranosylpurine,
6-(5-hydroxyfurfurylamino)-9-β-D-2'-deoxyribofuranosylpurine,
6-(3-methoxyfurfurylamino)-9-β-D-2'-deoxyribofuranosylpurine,
6-(4-methoxyfurfurylamino)-9-β-D-2'-deoxyribofuranosylpurine,
6-(5-methoxyfurfurylamino)-9-β-D-2'-deoxyribofuranosylpurine,
6-(2-aminofurfurylamino)-9-β-D-2'-deoxyribofuranosylpurine,
6-(3-aminofurfurylamino)-9-β-D-2'-deoxyribofuranosylpurine,
6-(4-aminofurfurylamino)-9-β-D-2'-deoxyribofuranosylpurine,
6-(3,4-dihydroxyfurfurylamino)-9-β-D-2'-deoxyribofuranosylpurine,
6-(3,5-dihydroxyfurfurylamino)-9-β-D-2'-deoxyribofuranosylpurine,
6-(3,4-dihydroxyfurfurylamino)-9-β-D-2'-deoxyribofuranosylpurine,
6-(2,4-dihydroxyfurfurylamino)-9-β-D-2'-deoxyribofuranosylpurine, 6-(2,5-dihydroxyfurfurylamino)-9-β-D-2'-deoxyribofuranosylpurine,
6-(2,6-dihydroxyfurfurylamino)-9-β-D-2'-deoxyribofuranosylpurine,
6-(3,4-dimethoxyfurfurylamino)-9-β-D-2'-deoxyribofuranosylpurine,
6-(3,4-dimethoxyfurfurylamino)-9-β-D-2'-deoxyribofuranosylpurine,
6-(3,5-dimethoxyfurfurylamino)-9-β-D-2'-deoxyribofuranosylpurine,
6-(2,3-dimethoxyfurfurylamino)-9-β-D-2'-deoxyribofuranosylpurine,
6-(2,4-dimethoxyfurfurylamino)-9-β-D-2'-deoxyribofuranosylpurine,
6-(2,5-dimethoxyfurfurylamino)-9-β-D-2'-deoxyribofuranosylpurine,
6-(2,6-dimethoxyfurfurylamino)-9-β-D-2'-deoxyribofuranosylpurine,
6-(2-hydroxy-3-methoxyfurfurylamino)-9-β-D-2'-deoxyribofuranosylpurine,
6-(2-hydroxy-4-methoxyfurfurylamino)-9-β-D-2'-deoxyribofuranosylpurine,
6-(2-hydroxy-5-methoxyfurfurylamino)-9-β-D-2'-deoxyribofuranosylpurine,
6-(2-hydroxy-6-methoxyfurfurylamino)-9-β-D-2'-deoxyribofuranosylpurine,
6-(3-hydroxy-2-methoxyfurfurylamino)-9-β-D-2'-deoxyribofuranosylpurine,
6-(3-hydroxy-4-methoxyfurfurylamino)-9-β-D-2'-deoxyribofuranosylpurine,
6-(3-hydroxy-5-methoxyfurfurylamino)-9-β-D-2'-deoxyribofuranosylpurine,
6-(3-hydroxy-6-methoxyfurfurylamino)-9-β-D-2'-deoxyribofuranosylpurine,
6-(4-hydroxy-2-methoxyfurfurylamino)-9-β-D-2'-deoxyribofuranosylpurine,
6-(4-hydroxy-3-methoxyfurfurylamino)-9-β-D-2'-deoxyribofuranosylpurine,
6-(4-hydroxy-5-methoxyfurfurylamino)-9-β-D-2'-deoxyribofuranosylpurine,
6-(4-hydroxy-6-methoxyfurfurylamino)-9-β-D-2'-deoxyribofuranosylpurine,
6-(2-fluorobenzylamino)-9-β-D-2'-deoxyribofuranosylpurine,
6-(3-fluorobenzylamino)-9-β-D-2'-deoxyribofuranosylpurine,
6-(4-fluorobenzylamino)-9-β-D-2'-deoxyribofuranosylpurine,
6-(2-bromobenzylamino)-9-β-D-2'-deoxyribofuranosylpurine,
6-(3-bromobenzylamino)-9-β-D-2'-deoxyribofuranosylpurine,
6-(4-bromobenzylamino)-9-β-D-2'-deoxyribofuranosylpurine,
6-(2-iodobenzylamino)-9-β-D-2'-deoxyribofuranosylpurine,
6-(3-iodobenzylamino)-9-β-D-2'-deoxyribofuranosylpurine,
6-(4-iodobenzylamino)-9-β-D-2'-deoxyribofuranosylpurine,
6-(2-chlorobenzylamino)-9-β-D-2'-deoxyribofuranosylpurine,
6-(2-chlorobenzylamino)-9-β-D-2'-deoxyribofuranosylpurine,
6-(3-chlorobenzylamino)-9-β-D-2'-deoxyribofuranosylpurine,
6-(4-chlorobenzylamino)-9-β-D-2'-deoxyribofuranosylpurine,
6-(2-aminobenzylamino)-9-β-D-2'-deoxyribofuranosylpurine,
6-(3-aminobenzylamino)-9-β-D-2'-deoxyribofuranosylpurine,
6-(4-aminobenzylamino)-9-β-D-2'-deoxyribofuranosylpurine,
6-(2-methoxybenzylamino)-9-β-D-2'-deoxyribofuranosylpurine,
6-(3-methoxybenzylamino)-9-β-D-2'-deoxyribofuranosylpurine,
6-(4-methoxybenzylamino)-9-β-D-2'-deoxyribofuranosylpurine, 6-(2-hydroxybenzylamino)-9-β-D-2'-deoxyribofuranosylpurine,
6-(3-hydroxybenzylamino)-9-β-D-2'-deoxyribofuranosylpurine,
6-(4-hydroxybenzylamino)-9-β-D-2'-deoxyribofuranosylpurine,
6-(3,4-dihydroxybenzylamino)-9-β-D-2'-deoxyribofuranosylpurine,
6-(3,5-dihydroxybenzylamino)-9-β-D-2'-deoxyribofuranosylpurine,
6-(3,4-dihydroxybenzylamino)-9-β-D-2'-deoxyribofuranosylpurine,
6-(2,4-dihydroxybenzylamino)-9-β-D-2'-deoxyribofuranosylpurine,
6-(2,5-dihydroxybenzylamino)-9-β-D-2'-deoxyribofuranosylpurine,
6-(2,6-dihydroxybenzylamino)-9-β-D-2'-deoxyribofuranosylpurine,
6-(3,4-dimethoxybenzylamino)-9-β-D-2'-deoxyribofuranosylpurine,
6-(3,4-dimethoxybenzylamino)-9-β-D-2'-deoxyribofuranosylpurine,
6-(3,5-dimethoxybenzylamino)-9-β-D-2'-deoxyribofuranosylpurine,
6-(2,3-dimethoxybenzylamino)-9-β-D-2'-deoxyribofuranosylpurine,
6-(2,4-dimethoxybenzylamino)-9-β-D-2'-deoxyribofuranosylpurine,
6-(2,5-dimethoxybenzylamino)-9-β-D-2'-deoxyribofuranosylpurine,
6-(2,6-dimethoxybenzylamino)-9-β-D-2'-deoxyribofuranosylpurine,
6-(2-hydroxy-3-methoxybenzylamino)-9-β-D-2'-deoxyribofuranosylpurine,
6-(2-hydroxy-4-methoxybenzylamino)-9-β-D-2'-deoxyribofuranosylpurine,
6-(2-hydroxy-5-methoxybenzylamino)-9-β-D-2'-deoxyribofuranosylpurine,
6-(2-hydroxy-6-methoxybenzylamino)-9-β-D-2'-deoxyribofuranosylpurine,
6-(3-hydroxy-2-methoxybenzylamino)-9-β-D-2'-deoxyribofuranosylpurine,
6-(3-hydroxy-4-methoxybenzylamino)-9-β-D-2'-deoxyribofuranosylpurine,
6-(3-hydroxy-5-methoxybenzylamino)-9-β-D-2'-deoxyribofuranosylpurine,
6-(3-hydroxy-6-methoxybenzylamino)-9-β-D-2'-deoxyribofuranosylpurine,
6-(4-hydroxy-2-methoxybenzylamino)-9-β-D-2'-deoxyribofuranosylpurine,
6-(4-hydroxy-3-methoxybenzylamino)-9-β-D-2'-deoxyribofuranosylpurine,
6-(4-hydroxy-5-methoxybenzylamino)-9-β-D-2'-deoxyribofuranosylpurine, 6-(4-hydroxy-6-methoxybenzylamino)-9-β-D-2'-deoxyribofuranosylpurine.

4. 6-aryl-9-glycosidpurine of formula Ia

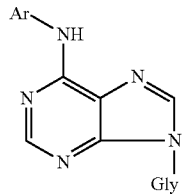

or a pharmaceutically acceptable salt thereof with alkali metal, ammonia, amine, or addition salt with acid, wherein Gly represents β-D-arabinofuranosyl, Ar represents benzyl or furfuryl, each of which is substituted by one or more substituents selected from the group comprising hydroxyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy.

5. 6-aryl-9-glycosidpurine according to claim 4, selected from the group consisting of, 6-(3-fluorofurfurylamino)-9-β-D-arabinofuranosylpurine,
6-(4-fluorofurfurylamino)-9-β-D-arabinofuranosylpurine,
6-(5-fluorofurfurylamino)-9-β-D-arabinofuranosylpurine,
6-(3-chlorofurfurylamino)-9-β-D-arabinofuranosylpurine,
6-(4-chlorofurfurylamino)-9-β-D-arabinofuranosylpurine,
6-(5-chlorofurfurylamino)-9-β-D-arabinofuranosylpurine,
6-(3-bromofurfurylamino)-9-β-D-arabinofuranosylpurine,
6-(4-bromofurfurylamino)-9-β-D-arabinofuranosylpurine,
6-(5-bromofurfurylamino)-9-β-D-arabinofuranosylpurine,
6-(3-hydroxyfurfurylamino)-9-β-D-arabinofuranosylpurine,
6-(4-hydroxyfurfurylamino)-9-β-D-arabinofuranosylpurine,
6-(5-hydroxyfurfurylamino)-9-β-D-arabinofuranosylpurine,
6-(3-methoxyfurfurylamino)-9-β-D-arabinofuranosylpurine,
6-(4-methoxyfurfurylamino)-9-β-D-arabinofuranosylpurine,
6-(5-methoxyfurfurylamino)-9-β-D-arabinofuranosylpurine,
6-(2-aminofurfurylamino)-9-β-D-arabinofuranosylpurine,
6-(3-aminofurfurylamino)-9-β-D-arabinofuranosylpurine,
6-(4-aminofurfurylamino)-9-β-D-arabinofuranosylpurine,
6-(3,4-dihydroxyfurfurylamino)-9-β-D-arabinofuranosylpurine,
6-(3,5-dihydroxyfurfurylamino)-9-β-D-arabinofuranosylpurine,
6-(3,4-dihydroxyfurfurylamino)-9-β-D-arabinofuranosylpurine,
6-(2,4-dihydroxyfurfurylamino)-9-β-D-arabinofuranosylpurine,
6-(2,5-dihydroxyfurfurylamino)-9-β-D-arabinofuranosylpurine,
6-(2,6-dihydroxyfurfurylamino)-9-β-D-arabinofuranosylpurine,
6-(3,4-dimethoxyfurfurylamino)-9-β-D-arabinofuranosylpurine,
6-(3,4-dimethoxyfurfurylamino)-9-β-D-arabinofuranosylpurine,
6-(3,5-dimethoxyfurfurylamino)-9-β-D-arabinofuranosylpurine,
6-(2,3-dimethoxyfurfurylamino)-9-β-D-arabinofuranosylpurine,
6-(2,4-dimethoxyfurfurylamino)-9-β-D-arabinofuranosylpurine,
6-(2,5-dimethoxyfurfurylamino)-9-β-D-arabinofuranosylpurine,
6-(2,6-dimethoxyfurfurylamino)-9-β-D-arabinofuranosylpurine,
6-(2-hydroxy-3-methoxyfurfurylamino)-9-β-D-arabinofuranosylpurine,
6-(2-hydroxy-4-methoxyfurfurylamino)-9-β-D-arabinofuranosylpurine,
6-(2-hydroxy-5-methoxyfurfurylamino)-9-β-D-arabinofuranosylpurine,
6-(2-hydroxy-6-methoxyfurfurylamino)-9-β-D-arabinofuranosylpurine,
6-(3-hydroxy-2-methoxyfurfurylamino)-9-β-D-arabinofuranosylpurine,
6-(3-hydroxy-4-methoxyfurfurylamino)-9-β-D-arabinofuranosylpurine,
6-(3-hydroxy-5-methoxyfurfurylamino)-9-β-D-arabinofuranosylpurine,
6-(3-hydroxy-6-methoxyfurfurylamino)-9-β-D-arabinofuranosylpurine,
6-(4-hydroxy-2-methoxyfurfurylamino)-9-β-D-arabinofuranosylpurine,
6-(4-hydroxy-3-methoxyfurfurylamino)-9-β-D-arabinofuranosylpurine,
6-(4-hydroxy-5-methoxyfurfurylamino)-9-β-D-arabinofuranosylpurine,
6-(4-hydroxy-6-methoxyfurfurylamino)-9-β-D-arabinofuranosylpurine,
6-(2-fluorobenzylamino)-9-β-D-arabinofuranosylpurine,
6-(3-fluorobenzylamino)-9-β-D-arabinofuranosylpurine,
6-(4-fluorobenzylamino)-9-β-D-arabinofuranosylpurine,
6-(2-bromobenzylamino)-9-β-D-arabinofuranosylpurine,
6-(3-bromobenzylamino)-9-β-D-arabinofuranosylpurine,
6-(4-bromobenzylamino)-9-β-D-arabinofuranosylpurine,
6-(2-iodobenzylamino)-9-β-D-arabinofuranosylpurine,
6-(3-iodobenzylamino)-9-β-D-arabinofuranosylpurine,
6-(4-iodobenzylamino)-9-β-D-arabinofuranosylpurine,
6-(2-chlorobenzylamino)-9-β-D-arabinofuranosylpurine,
6-(2-chlorobenzylamino)-9-β-D-arabinofuranosylpurine,
6-(3-chlorobenzylamino)-9-β-D-arabinofuranosylpurine,
6-(4-chlorobenzylamino)-9-β-D-arabinofuranosylpurine,
6-(2-methoxybenzylamino)-9-β-D-arabinofuranosylpurine,
6-(3-methoxybenzylamino)-9-β-D-arabinofuranosylpurine,
6-(4-methoxybenzylamino)-9-β-D-arabinofuranosylpurine,
6-(2-hydroxybenzylamino)-9-β-D-arabinofuranosylpurine, 6-(3-hydroxybenzylamino)-9-β-D-arabinofuranosylpurine,
6-(4-hydroxybenzylamino)-9-β-D-arabinofuranosylpurine,
6-(4-hexylbenzylamino)-9-β-D-arabinofuranosylpurine,
6-(2-fluoro-6-(trifluoromethyl)benzylamino)-9-β-D-arabinofuranosylpurine,
6-(3-chloro-2,6-difluorobenzylamino)-9-β-D-arabinofuranosylpurine,
6-(3-(trifluoromethylthio)benzylamino)-9-β-D-arabinofuranosylpurine,
6-(2-chloro-3,6-difluorobenzylamino)-9-β-D-arabinofuranosylpurine,
6-(4-(trifluoromethylthio)benzylamino)-9-β-D-arabinofuranosylpurine,
6-(3-fluoro-5-(trifluoromethyl)benzylamino)-9-β-D-arabinofuranosylpurine,
6-(2-chloro-4-fluorobenzylamino)-9-β-D-arabinofuranosylpurine,
6-(2-(trifluoromethoxy)benzylamino)-9-β-D-arabinofuranosylpurine,
6-(3-(trifluoromethyl)benzylamino)-9-β-D-arabinofuranosylpurine,
6-(2-(trifluoromethyl)benzylamino)-9-β-D-arabinofuranosylpurine,
6-(4-(trifluoromethyl)benzylamino)-9-β-D-arabinofuranosylpurine,
6-(4-chloro-3-(trifluoromethyl)benzylamino)-9-β-D-arabinofuranosylpurine,
6-(4-fluoro-3-(trifluoromethyl)benzylamino)-9-β-D-arabinofuranosylpurine,
6-(3,5-bis(trifluoromethyl)benzylamino)-9-β-D-arabinofuranosylpurine,
6-(3-(trifluoromethoxy)benzylamino)-9-β-D-arabinofuranosylpurine,
6-(4-(trifluoromethoxy)benzylamino)-9-β-D-arabinofuranosylpurine,
6-(4-(trifluoromethyl)benzylamino)-9-β-D-arabinofuranosylpurine,
6-(2-aminobenzylamino)-9-β-D-arabinofuranosylpurine,
6-(3-aminobenzylamino)-9-β-D-arabinofuranosylpurine,
6-(4-aminobenzylamino)-9-β-D-arabinofuranosylpurine,
6-(4-diethylaminobenzylamino)-9-β-D-arabinofuranosylpurine,
6-(3,4-dihydroxybenzylamino)-9-β-D-arabinofuranosylpurine,
6-(3,5-dihydroxybenzylamino)-9-β-D-arabinofuranosylpurine,
6-(3,4-dihydroxybenzylamino)-9-β-D-arabinofuranosylpurine,
6-(2,4-dihydroxybenzylamino)-9-β-D-arabinofuranosylpurine,
6-(2,5-dihydroxybenzylamino)-9-β-D-arabinofuranosylpurine,
6-(2,6-dihydroxybenzylamino)-9-β-D-arabinofuranosylpurine,
6-(3,4-dimethoxybenzylamino)-9-β-D-arabinofuranosylpurine,
6-(3,4-dimethoxybenzylamino)-9-β-D-arabinofuranosylpurine,
6-(3,5-dimethoxybenzylamino)-9-β-D-arabinofuranosylpurine,
6-(2,3-dimethoxybenzylamino)-9-β-D-arabinofuranosylpurine,
6-(2,4-dimethoxybenzylamino)-9-β-D-arabinofuranosylpurine,
6-(2,5-dimethoxybenzylamino)-9-β-D-arabinofuranosylpurine,
6-(2,6-dimethoxybenzylamino)-9-β-D-arabinofuranosylpurine,
6-(2-hydroxy-3-methoxybenzylamino)-9-β-D-arabinofuranosylpurine,
6-(2-hydroxy-4-methoxybenzylamino)-9-β-D-arabinofuranosylpurine,
6-(2-hydroxy-5-methoxybenzylamino)-9-β-D-arabinofuranosylpurine,
6-(2-hydroxy-6-methoxybenzylamino)-9-β-D-arabinofuranosylpurine,
6-(3-hydroxy-2-methoxybenzylamino)-9-β-D-arabinofuranosylpurine,
6-(3-hydroxy-4-methoxybenzylamino)-9-β-D-arabinofuranosylpurine,
6-(3-hydroxy-5-methoxybenzylamino)-9-β-D-arabinofuranosylpurine,
6-(3-hydroxy-6-methoxybenzylamino)-9-β-D-arabinofuranosylpurine,
6-(4-hydroxy-2-methoxybenzylamino)-9-β-D-arabinofuranosylpurine,
6-(4-hydroxy-3-methoxybenzylamino)-9-β-D-arabinofuranosylpurine,
6-(4-hydroxy-5-methoxybenzylamino)-9-β-D-arabinofuranosylpurine,
6-(4-hydroxy-6-methoxybenzylamino)-9-β-D-arabinofuranosylpurine,
6-(2,3,4-trimethoxybenzylamino)-9-β-D-arabinofuranosylpurine,
6-(2,4,5-trimethoxybenzylamino)-9-β-D-arabinofuranosylpurine,
6-(2,4,6-trimethoxybenzylamino)-9-β-D-arabinofuranosylpurine,
6-(3,4,5-trimethoxybenzylamino)-9-β-D-arabinofuranosylpurine,
6-(2-hydroxy-3,4,5-trimethoxybenzylamino)-9-β-D-arabinofuranosylpurine,
6-(2-hydroxy-3,4,6-trimethoxybenzylamino)-9-β-D-arabinofuranosylpurine,
6-(2-hydroxy-4,5,6-trimethoxybenzylamino)-9-β-D-arabinofuranosylpurine,
6-(2,4,6-trimethoxybenzylamino)-9-β-D-arabinofuranosylpurine,
6-(2,3,4-trihydroxybenzylamino)-9-β-D-arabinofuranosylpurine,
6-(2,4,6-trihydroxybenzylamino)-9-β-D-arabinofuranosylpurine,
6-(2,3,4-trihydroxybenzylamino)-9-β-D-arabinofuranosylpurine,
6-(3,4,5-trihydroxybenzylamino)-9-β-D-arabinofuranosylpurine,
6-(2,4,6-trihydroxybenzylamino)-9-β-D-arabinofuranosylpurine,
6-(2-hydroxy-3-chlorobenzylamino)-9-β-D-arabinofuranosylpurine,
6-(2-hydroxy-4-chlorobenzylamino)-9-β-D-arabinofuranosylpurine,
6-(2-hydroxy-5-chlorobenzylamino)-9-β-D-arabinofuranosylpurine,
6-(2-hydroxy-6-chlorobenzylamino)-9-β-D-arabinofuranosylpurine,
6-(2-hydroxy-3-iodobenzylamino)-9-β-D-arabinofuranosylpurine,
6-(2-hydroxy-4-iodobenzylamino)-9-β-D-arabinofuranosylpurine, 6-(2-hydroxy-5-iodobenzylamino)-9-β-D-arabinofuranosylpurine,
6-(2-hydroxy-6-iodobenzylamino)-9-β-D-arabinofuranosylpurine,
6-(2-hydroxy-3-bromobenzylamino)-9-β-D-arabinofuranosylpurine,
6-(2-hydroxy-4-bromobenzylamino)-9-β-D-arabinofuranosylpurine,
6-(2-hydroxy-5-bromobenzylamino)-9-β-D-arabinofuranosylpurine,
6-(2-hydroxy-6-bromobenzylamino)-9-β-D-arabinofuranosylpurine,
6-(2-hydroxy-3-fluorobenzylamino)-9-β-D-arabinofuranosylpurine,
6-(2-hydroxy-4-fluorobenzylamino)-9-β-D-arabinofuranosylpurine,
6-(2-hydroxy-5-fluorobenzylamino)-9-β-D-arabinofuranosylpurine.

6. The method of claim 1, wherein the regulation of aging is inhibition of aging.

7. The method of claim 1, wherein the animal is a mammal.

8. The method of claim 1, wherein Ar represents benzyl or furfuryl, each of which can be substituted by one to three substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy.

9. The method of claim 2, wherein Ar represents benzyl or furfuryl, each of which can be substituted by one to three substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy.

10. 6-aryl-9-glycosidpurine of claim 4, wherein Ar represents benzyl or furfuryl, each of which can be substituted by one to three substituents selected from the group comprising hydroxyl, alkyl, halogen, alkoxy, amino, mercapto, carboxyl, cyano, amido, sulfo, sulfamido, acyl, acylamino, acyloxy, alkylamino, dialkylamino, alkylmercapto, trifluoromethyl, trifluoromethoxy.

* * * * *